United States Patent
Newcombe et al.

(10) Patent No.: US 7,442,697 B2
(45) Date of Patent: *Oct. 28, 2008

(54) 4-IMIDAZOLYL SUBSTITUTED PYRIMIDINE DERIVATIVES WITH CDK INHIBITORY ACTIVITY

(75) Inventors: Nicholas John Newcombe, Macclesfield (GB); Andrew Peter Thomas, Macclesfield (GB)

(73) Assignee: AstraZeneca AB, Sodertaje (SE)

( * ) Notice: Subject to any disclaimer, the term of this patent is extended or adjusted under 35 U.S.C. 154(b) by 461 days.

This patent is subject to a terminal disclaimer.

(21) Appl. No.: 10/507,169

(22) PCT Filed: Mar. 6, 2003

(86) PCT No.: PCT/GB03/00935

§ 371 (c)(1),
(2), (4) Date: Sep. 9, 2004

(87) PCT Pub. No.: WO03/076434

PCT Pub. Date: Sep. 18, 2003

(65) Prior Publication Data

US 2006/0074096 A1    Apr. 6, 2006

(30) Foreign Application Priority Data

Mar. 9, 2002 (GB) ................... 0205695.0
Jul. 31, 2002 (GB) ................... 0217633.7

(51) Int. Cl.
*C07D 403/04* (2006.01)
*A61K 31/505* (2006.01)

(52) U.S. Cl. ............... 514/235.8; 514/255.05; 514/275; 544/122; 544/331

(58) Field of Classification Search ........... 544/122, 544/331; 514/235.8, 255.05, 275
See application file for complete search history.

(56) References Cited

U.S. PATENT DOCUMENTS

| | | | |
|---|---|---|---|
| 4,983,608 A | 1/1991 | Effland et al. | |
| 5,516,775 A | 5/1996 | Zimmermann et al. | |
| 5,521,184 A | 5/1996 | Zimmermann | |
| 5,610,303 A | 3/1997 | Kimura et al. | |
| 5,739,143 A | 4/1998 | Adams et al. | |
| 5,859,041 A | 1/1999 | Liverton et al. | |
| 6,835,726 B2 | 12/2004 | Cushing et al. | |
| 6,908,920 B2 | 6/2005 | Thomas et al. | |
| 6,969,714 B2 * | 11/2005 | Breault et al. | 514/235.8 |
| 2003/0144303 A1 | 7/2003 | Hawley et al. | |
| 2003/0191307 A1 | 10/2003 | Blumenkopf et al. | |
| 2004/0102630 A1 | 5/2004 | Brumby et al. | |
| 2004/0224966 A1 | 11/2004 | Brumby et al. | |
| 2005/0176743 A1 | 8/2005 | Luecking et al. | |
| 2006/0079543 A1 | 4/2006 | Sum et al. | |
| 2006/0111378 A1 | 5/2006 | Cleve et al. | |

FOREIGN PATENT DOCUMENTS

| | | |
|---|---|---|
| CA | 2231765 | 9/1998 |
| EP | 0 135 472 | 3/1985 |
| EP | 0 363 002 | 4/1990 |
| EP | 0 379 806 A2 | 8/1990 |
| EP | 0 945 443 A1 | 9/1999 |
| EP | 1056742 | 7/2003 |
| HU | 220630 | 3/2002 |
| WO | 91/18887 | 12/1991 |
| WO | 92/20642 | 11/1992 |
| WO | 95/09847 | 4/1995 |
| WO | 95/09851 | 4/1995 |
| WO | 95/09852 | 4/1995 |
| WO | 95/09853 | 4/1995 |
| WO | 95/15952 | 6/1995 |
| WO | 96/05177 | 2/1996 |
| WO | 96/28427 | 9/1996 |
| WO | 96/40143 | 12/1996 |
| WO | 97/19065 | 5/1997 |
| WO | 97/35856 | 10/1997 |
| WO | 97/40017 | 10/1997 |
| WO | 97/44326 | 11/1997 |
| WO | 97/47618 | 12/1997 |
| WO | 98/11095 | 3/1998 |
| WO | 98/16230 | 4/1998 |
| WO | 98/18782 | 5/1998 |
| WO | 98/25619 | 6/1998 |
| WO | 98/33798 | 8/1998 |
| WO | 98/41512 | 9/1998 |
| WO | 98/54093 | 12/1998 |
| WO | 98/56788 | 12/1998 |
| WO | 99/01136 | 1/1999 |
| WO | 99/32121 | 1/1999 |
| WO | 99/18096 | 4/1999 |
| WO | 99/18942 | 4/1999 |
| WO | 99/31073 | 6/1999 |
| WO | 99/41253 | 8/1999 |
| WO | 99/50250 | 10/1999 |
| WO | 99/50251 | 10/1999 |
| WO | 00/12485 | 3/2000 |

(Continued)

OTHER PUBLICATIONS

Traxler, Protein tyrosine kinase inhibitors in cancer treatment, Expert Opinion on Therapeutic Patents, 7(6), pp. 571-588, 1997.*

(Continued)

*Primary Examiner*—Deepak Rao
(74) *Attorney, Agent, or Firm*—Morgan, Lewis & Bockius LLP

(57) ABSTRACT

Compounds of the formula (I): wherein $R^1$, $R^2$, $R^3$, $R^4$, $R^5$ and p are as defined within and a pharmaceutically acceptable salts and in vivo hydrolysable esters are described. Also described are processes for their preparation and their use as medicaments, particularly medicaments for producing a cell cycle inhibitory (anti-cell-proliferation) effect in a warm-blooded animal, such as man.

11 Claims, No Drawings

FOREIGN PATENT DOCUMENTS

| | | |
|---|---|---|
| WO | 00/12486 | 3/2000 |
| WO | 00/17202 | 3/2000 |
| WO | 00/17203 | 3/2000 |
| WO | 00/21926 | 4/2000 |
| WO | 00/25780 | 5/2000 |
| WO | 00/26209 | 5/2000 |
| WO | 00/39101 | 6/2000 |
| WO | 00/44750 | 8/2000 |
| WO | 00/49018 | 8/2000 |
| WO | 00/53595 A | 9/2000 |
| WO | 00/55161 | 9/2000 |
| WO | 00/59892 | 10/2000 |
| WO | 00/78731 A1 | 12/2000 |
| WO | 01/14375 A | 3/2001 |
| WO | 01/29009 A1 | 4/2001 |
| WO | 01/30778 A1 | 5/2001 |
| WO | 01/37835 A | 5/2001 |
| WO | 01/47897 A1 | 7/2001 |
| WO | 01/47921 A1 | 7/2001 |
| WO | 01/60816 A1 | 8/2001 |
| WO | 01/64653 A1 | 9/2001 |
| WO | 01/64654 A | 9/2001 |
| WO | 01/64655 A1 | 9/2001 |
| WO | 01/64656 A1 | 9/2001 |
| WO | 01/72717 A1 | 10/2001 |
| WO | 02/04429 A | 1/2002 |
| WO | 02/20512 A | 3/2002 |
| WO | WO 02/046170 | 6/2002 |
| WO | WO 02/046171 | 6/2002 |
| WO | 02/066481 A1 | 8/2002 |
| WO | WO 02/065979 | 8/2002 |
| WO | WO 02/066480 | 8/2002 |
| WO | WO 02/092573 | 11/2002 |
| WO | 02/096887 A1 | 12/2002 |
| WO | WO 02/096888 | 12/2002 |
| WO | 03/007955 A2 | 1/2003 |
| WO | WO 03/011837 | 2/2003 |
| WO | WO 03/029249 | 4/2003 |
| WO | WO 03/031446 | 4/2003 |
| WO | WO 03/037891 | 5/2003 |
| WO | 03/076433 A1 | 9/2003 |
| WO | 03/076435 A1 | 9/2003 |
| WO | 03/076436 A1 | 9/2003 |
| WO | WO 2004/005283 | 1/2004 |
| WO | WO 2004/043467 | 5/2004 |
| WO | WO 2004/043953 | 5/2004 |
| WO | WO 2004/087698 | 10/2004 |
| WO | WO 2004/087699 | 10/2004 |
| WO | WO 2004/101549 | 11/2004 |
| WO | WO 2004/101564 | 11/2004 |
| WO | WO 2005/012298 | 2/2005 |
| WO | WO 2005/037800 | 4/2005 |
| WO | WO 2005/075461 | 8/2005 |
| WO | WO 2005/075468 | 8/2005 |
| WO | WO 2005/113550 | 12/2005 |
| WO | WO 2005/116025 | 12/2005 |
| WO | WO 2006/034872 | 4/2006 |
| WO | WO 2006/044509 | 4/2006 |
| WO | WO 2006/050076 | 5/2006 |
| WO | WO 2006/064251 | 6/2006 |
| WO | WO 2006/075152 | 7/2006 |
| WO | WO 2006/095159 | 9/2006 |
| WO | WO 2007/015064 | 2/2007 |
| WO | WO 2007/036732 | 4/2007 |
| WO | WO 2007/040440 | 4/2007 |
| WO | WO 2007/138268 | 12/2007 |
| WO | WO 2007/138277 | 12/2007 |
| WO | WO 2007/148070 | 12/2007 |

OTHER PUBLICATIONS

Lu Valle et al., Cell Cycle Control in Growth Plate Chondrocytes, Frontiers in Biosciences 5, d493-503, May 2000.*
Boschelli et al., Synthesis and Tyrosine Kinase Inhibitory Activity of a Series of 2-Amino-8-$H$-pyrido[2,3-$d$]pyrimidines: Identifidation of Potent, Selective Platelet-Derived Growth Factor Receptor Tyrosine Kinase Inhibitors, J. Med. Chem., vol. 41, 1998, pp. 4365-4377.
Deady et al., "Reactions of some Quinazoline Compounds with Ethoxymethylenemalonic Acid Derivatives", J. Heterocyclic Chem., vol. 26, 1989, pp. 161-168.
El-Kerdawy et al.; "2,4-Bis (Substituted)-5-Nitropyrimidines of Expected Diuretic Action"; Egypt J. Chem. vol. 29, No. 2, 1986, pp. 247-251.
Fiziol Akt Veshchestva, 1975, vol. 7, pp. 68-72.
Ghosh et al.; "2,4-Bis(arylamino)-5-methylpyrimidines as Antimicrobial Agents"; J. Med. Chem., 1967, vol. 10, No. 5, pp. 974-975.
Ghosh, "2,4-Bis(Arylamino)-6-Methyl Pyrimidines as Antimicrobial Agents", J. Indian Chem. Soc., vol. 58, No. 5, 1981, pp. 512-513.
Schmidt et al.; "A Convenient Synthesis of 2-substituted 4-Amino-5-pyrimidinecarbonitriles"; J. Heterocycle Chem., 1997, vol. 24, No. 5, pp. 1305-1307.
Zimmermann et al., Phenylamino-Pyrimidine (PAP) Derivatives: A New Class of Potent and Selective Inhibitors of Protein Kinase C (PKC), Arch. Pharm. Pharm. Med. Chem., vol. 329, 1996, pp. 371-376.
Blain et al. "Differential Interaction of the Cyclin-dependent Kinase (Cdk) inhibitor p27Kip1 with Cyclin A-Cdk2 and Cyclin D2-Cdk4" J. Biol. Chem. 272(41): 25863-25872 (1997).
Simone, Oncology: Introduction, Cecil Textbook of Medicine, 20th Edition, vol. 1, pp. 1004-1010 (1996).
Volin et al. "Cell cycle implications in the pathogenesis of rheumatoid arthritis" Frontiers in Bioscience 5: D594-601(2000).
Fiziol Akt Veshchestva 7:68-72 (1975) (Translation enclosed).

* cited by examiner

4-IMIDAZOLYL SUBSTITUTED PYRIMIDINE DERIVATIVES WITH CDK INHIBITORY ACTIVITY

This application is a 371 of PCT/GB03/00935 filed Mar. 6, 2003.

The invention relates to pyrimidine derivatives, or pharmaceutically acceptable salts or in vivo hydrolysable esters thereof, which possess cell-cycle inhibitory activity and are accordingly useful for their anti-cell-proliferation (such as anti-cancer) activity and are therefore useful in methods of treatment of the human or animal body. The invention also relates to processes for the manufacture of said pyrimidine derivatives, to pharmaceutical compositions containing them and to their use in the manufacture of medicaments of use in the production of an anti-cell-proliferation effect in a warm-blooded animal such as man.

A family of intracellular proteins called cyclins play a central role in the cell cycle. The synthesis and degradation of cyclins is tightly controlled such that their level of expression fluctuates during the cell cycle. Cyclins bind to cyclin-dependent serine/threonine kinases (CDKs) and this association is essential for CDK (such as CDK1, CDK2, CDK4 and/or CDK6) activity within the cell. Although the precise details of how each of these factors combine to regulate CDK activity is poorly understood, the balance between the two dictates whether or not the cell will progress through the cell cycle.

The recent convergence of oncogene and tumour suppressor gene research has identified regulation of entry into the cell cycle as a key control point of mitogenesis in tumours. Moreover, CDKs appear to be downstream of a number of oncogene signalling pathways. Disregulation of CDK activity by upregulation of cyclins and/or deletion of endogenous inhibitors appears to be an important axis between mitogenic signalling pathways and proliferation of tumour cells.

Accordingly it has been recognised that an inhibitor of cell cycle kinases, particularly inhibitors of CDK2, CDK4 and/or CDK6 (which operate at the S-phase, G1-S and G1-S phase respectively) should be of value as a selective inhibitor of cell proliferation, such as growth of mammalian cancer cells.

The present invention is based on the discovery that certain pyrimidine compounds surprisingly inhibit the effects of cell cycle kinases showing selectivity for CDK2, CDK4 and CDK6, and thus possess anti-cell-proliferation properties. Such properties are expected to be of value in the treatment of disease states associated with aberrant cell cycles and cell proliferation such as cancers (solid tumours and leukemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Accordingly, the present invention provides a compound of formula (I):

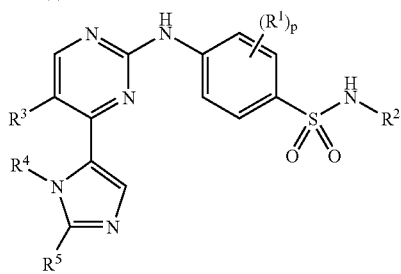

wherein:

$R^1$ is halo, cyano, $C_{1-3}$alkyl or $C_{1-3}$alkoxy;

p is 0-2; wherein the values of $R^1$ may be the same or different;

$R^2$ is hydrogen, $C_{1-4}$alkyl, $C_{2-4}$alkenyl, $C_{2-4}$alkynyl, $C_{3-6}$cycloalkyl, $C_{3-6}$cycloalkylC$_{1-3}$alkyl, a heterocyclyl or heterocyclylC$_{1-3}$alkyl; wherein $R^2$ may be optionally substituted on carbon by one or more hydroxy, methyl, ethyl, methoxy, ethoxy, propoxy, trifluoromethyl, trifluoromethoxy, 2,2,2-trifluoroethoxy or cyclopropylmethoxy; and wherein if said heterocyclyl contains an —NH— moiety that nitrogen may be optionally substituted by one or more methyl, ethyl, acetyl, 2,2,2-trifluoroethyl or methoxyethyl;

$R^3$ is hydrogen, halo or cyano;

$R^4$ is $C_{1-6}$alkyl or $C_{1-6}$alkoxyC$_{1-6}$alkyl;

$R^5$ is substituted methyl, optionally substituted $C_{2-4}$alkyl, $C_{3-6}$cycloalkyl or optionally substituted $C_{2-6}$alkenyl; wherein said substituents are selected from one or more hydroxy, methoxy, ethoxy, propoxy, isopropoxy, trifluoromethyl, trifluoromethoxy, 2,2,2-trifluoroethoxy, phenyl, methylamino, ethylamino, dimethylamino, diethylamino, methylthio, ethylthio, propylthio, isopropylthio, methylsulphinyl, ethylsulphinyl, propylsulphinyl, isopropylsulphinyl, methylsulphonyl, ethylsulphonyl, propylsulphonyl, isopropylsulphonyl or cyclopropylmethoxy;

or a pharmaceutically acceptable salt or an in vivo hydrolysable ester thereof; provided that the compound is not 4-(1-methyl-2-ethylimidazol-5-yl)-2-{4-[N-(tetrahydrofur-2-yl-methyl)sulphamoyl]anilino}pyrimidine; 4-(1-methyl-2-ethyl-imidazol-5-yl)-2-{4-[N-(2-methoxyethyl)sulphamoyl]anilino}pyrimidine; 4-(1-methyl-2-isopropyl-imidazol-5-yl)-2-{4-[N-(2-methoxyethyl)sulphamoyl]anilino}pyrimidine; 4-(1-methyl-2-isopropyl-imidazol-5-yl)-2-{4-[N-(cyclopropylmethyl)sulphamoyl]anilino}pyrimidine; 4-(1-methyl-2-isopropyl-imidazol-5-yl)-2-{4-[N-(tetrahydrofur-2-ylmethyl)sulphamoyl]anilino}pyrimidine; 4-(1-methyl-2-ethylimidazol-5-yl)-2-{4-[N-(cyclopropylmethyl)sulphamoyl]anilino}pyrimidine; 4-(1-methyl-2-ethyl-imidazol-5-yl)-2-[4-(N-cyclopropyl-sulphamoyl)anilino]pyrimidine; 4-(1-methyl-2-ethylimidazol-5-yl)-2-[4-(N-cyclobutyl-sulphamoyl)anilino]pyrimidine; or 4-(1-methyl-2-methoxymethylimidazol-5-yl)-2-{4-[N-(2-methoxyethyl) sulphamoyl]anilino}pyrimidine.

According to a further feature of the present invention there is provided a compound of formula (I) (as depicted above) wherein:

$R^1$ is halo, cyano, $C_{1-3}$alkyl or $C_{1-3}$alkoxy;

p is 0-2; wherein the values of $R^1$ may be the same or different;

$R^2$ is $C_{1-4}$alkyl, $C_{2-4}$alkenyl, $C_{2-4}$alkynyl, $C_{3-6}$cycloalkyl, $C_{3-6}$cycloalkylC$_{1-3}$alkyl, a heterocyclyl or heterocyclylC$_{1-3}$alkyl; wherein $R^2$ may be optionally substituted on carbon by one or more methyl, ethyl, methoxy, ethoxy, propoxy, trifluoromethyl, trifluoromethoxy, 2,2,2-trifluoroethoxy or cyclopropylmethoxy; and wherein if said heterocyclyl contains an —NH— moiety that nitrogen may be optionally substituted by one or more methyl, ethyl, acetyl, 2,2,2-trifluoroethyl or methoxyethyl;

$R^3$ is hydrogen, halo or cyano;

$R^4$ is $C_{1-6}$alkyl or $C_{1-6}$alkoxyC$_{1-6}$alkyl;

$R^5$ is substituted methyl, optionally substituted $C_{2-6}$alkyl or optionally substituted $C_{2-6}$alkenyl; wherein said substituents are selected from one or more methoxy, ethoxy, propoxy, trifluoromethyl, trifluoromethoxy, 2,2,2-trifluoroethoxy or cyclopropylmethoxy; or a pharmaceutically acceptable salt or an in vivo hydrolysable ester thereof; provided that the compound is not 4-(1-methyl-2-ethylimidazol-5-yl)-2-{4-[N-(tetrahydrofur-2-ylmethyl)sulphamoyl]anilino}pyrimidine; 4-(1-methyl-2-ethyl-imidazol-5-yl)-2-{4-[N-(2-methoxyethyl)sulphamoyl]anilino}pyrimidine; 4-(1-methyl-2-isopropyl-imidazol-5-yl)-2-{4-[N-(2-methoxyethyl)sulphamoyl]anilino}pyrimidine; 4-(1-methyl-2-isopropyl-imidazol-5-yl)-2-{4-[N-(cyclopropylmethyl)sulphamoyl]anilino}pyrimidine; 4-(1-methyl-2-isopropyl-imidazol-5-yl)-2-{4-[N-(tetrahydrofur-2-ylmethyl)sulphamoyl]anilino}pyrimidine; 4-(1-methyl-2-ethylimidazol-5-yl)-2-{4-[N-(cyclopropylmethyl)sulphamoyl]anilino}pyrimidine; 4-(1-methyl-2-trifluoromethylimidazol-5-yl)-2-{4[N-(tetrahydrofur-2-ylmethyl)sulphamoyl]anilino}pyrimidine; 4-(1-methyl-2-ethyl-imidazol-5-yl)-2-[4-(N-cyclopropylsulphamoyl)anilino]pyrimidine; 4-(1-methyl-2-ethylimidazol-5-yl)-2-[4-(N-cyclobutyl-sulphamoyl)anilino]pyrimidine; or 4-(1-methyl-2-methoxymethylimidazol-5-yl)-2-{4-[N-(2-methoxyethyl) sulphamoyl]anilino}pyrimidine.

According to a further feature of the present invention there is provided a compound of formula (I) (as depicted above) wherein:

$R^1$ is halo, cyano, $C_{1-3}$alkyl or $C_{1-3}$alkoxy;

p is 0-2; wherein the values of $R^1$ may be the same or different;

$R^2$ is $C_{1-4}$alkyl, $C_{2-4}$alkenyl, $C_{2-4}$alkynyl, $C_{3-6}$cycloalkyl, $C_{3-6}$cycloalkyl$C_{1-3}$alkyl, a heterocyclyl or heterocyclyl$C_{1-3}$alkyl; wherein $R^2$ may be optionally substituted on carbon by one or more methyl, ethyl, methoxy, ethoxy, propoxy, trifluoromethyl, trifluoromethoxy, 2,2,2-trifluoroethoxy or cyclopropylmethoxy; and wherein if said heterocyclyl contains an —NH— moiety that nitrogen may be optionally substituted by one or more methyl, ethyl, acetyl, 2,2,2-trifluoroethyl or methoxyethyl;

$R^3$ is hydrogen, halo or cyano;

$R^4$ is $C_{1-6}$alkyl or $C_{1-6}$alkoxy$C_{1-6}$alkyl;

$R^5$ is substituted methyl, optionally substituted $C_{2-6}$alkyl, $C_{3-6}$cycloalkyl or optionally substituted $C_{2-6}$alkenyl; wherein said substituents are selected from one or more hydroxy, methoxy, ethoxy, propoxy, trifluoromethyl, trifluoromethoxy, 2,2,2-trifluoroethoxy or cyclopropylmethoxy;

or a pharmaceutically acceptable salt or an in vivo hydrolysable ester thereof; provided that the compound is not 4-(1-methyl-2-ethylimidazol-5-yl)-2-{4-[N-(tetrahydrofur-2-yl-methyl)sulphamoyl]anilino}pyrimidine; 4-(1-methyl-2-ethyl-imidazol-5-yl)-2-{4-[N-(2-methoxyethyl)sulphamoyl]anilino}pyrimidine; 4-(1-methyl-2-isopropyl-imidazol-5-yl)-2-{4-[N-(2-methoxyethyl)sulphamoyl]anilino}pyrimidine; 4-(1-methyl-2-isopropyl-imidazol-5-yl)-2-{4-[N-(cyclopropylmethyl)sulphamoyl]anilino}pyrimidine; 4-(1-methyl-2-isopropyl-imidazol-5-yl)-2-{4-[N-(tetrahydrofur-2-ylmethyl)sulphamoyl]anilino}pyrimidine; 4-(1-methyl-2-ethylimidazol-5-yl)-2-{4-[N-(cyclopropylmethyl)sulphamoyl]anilino}pyrimidine; 4-(1-methyl-2-trifluoromethylimidazol-5-yl)-2-{4-[N-(tetrahydrofur-2-ylmethyl)sulphamoyl]anilino}pyrimidine; 4-(1-methyl-2-ethyl-imidazol-5-yl)-2-[4-(N-cyclopropylsulphamoyl)anilino]pyrimidine; 4-(1-methyl-2-ethylimidazol-5-yl)-2-[4-(N-cyclobutyl-sulphamoyl)anilino]pyrimidine; or 4-(1-methyl-2-methoxymethylimidazol-5-yl)-2-{4-[N-(2-methoxyethyl) sulphamoyl]anilino}pyrimidine.

In this specification the term "alkyl" includes both straight and branched chain alkyl groups but references to individual alkyl groups such as "propyl" are specific for the straight chain version only. For example, "$C_{1-6}$alkyl", "$C_{2-6}$alkyl", "$C_{1-4}$alkyl" and "$C_{1-3}$alkyl" include propyl, isopropyl and t-butyl. However, references to individual alkyl groups such as 'propyl' are specific for the straight chained version only and references to individual branched chain alkyl groups such as 'isopropyl' are specific for the branched chain version only. A similar convention applies to other radicals, for example "$C_{3-6}$cycloalkyl$C_{1-3}$alkyl" includes cyclopropylmethyl, 1-cyclobutylethyl and 3-cyclopropylpropyl. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

A "heterocyclyl" is a saturated, partially saturated or unsaturated, monocyclic ring containing 4-6 atoms of which at least one atom is chosen from nitrogen, sulphur or oxygen, which may, unless otherwise specified, be carbon or nitrogen linked, and a ring sulphur atom may be optionally oxidised to form the S-oxide(s). Examples and suitable values of the term "heterocyclyl" are morpholino, piperidyl, pyridyl, pyranyl, pyrrolyl, isothiazolyl, thienyl, thiadiazolyl, piperazinyl, thiazolidinyl, thiomorpholino, pyrrolinyl, tetrahydropyranyl, tetrahydrofuryl, imidazolyl, pyrimidyl, pyrazinyl, pyridazinyl and isoxazolyl. Suitably a "heterocyclyl" is tetrahydrofuryl.

Examples of "$C_{1-3}$alkoxy" include methoxy, ethoxy and propoxy. Examples of "$C_{2-6}$alkenyl" and "$C_{2-4}$alkenyl" are vinyl, allyl and 1-propenyl. Examples of "$C_{2-4}$alkynyl" are ethynyl, 1-propynyl and 2-propynyl. Examples of "$C_{3-6}$cycloalkyl" are cyclopropyl, cyclobutyl, cyclopentyl and cyclohexyl. Examples of "heterocyclyl$C_{1-3}$alkyl" include pyridylmethyl, 3-morpholinopropyl and 2-pyrimid-2-ylethyl. Examples of "$C_{1-6}$alkoxy$C_{1-6}$alkyl" and "$C_{1-4}$alkoxy$C_{1-4}$alkyl" are methoxymethyl, 2-methoxyethyl and 2-ethoxypropyl.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

An in vivo hydrolysable ester of a compound of the formula (I) containing carboxy or hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

Some compounds of the formula (I) may have chiral centres and/or geometric isomeric centres (E- and Z-isomers), and it is to be understood that the invention encompasses all such optical, diastereoisomers and geometric isomers that possess CDK inhibitory activity.

The invention relates to any and all tautomeric forms of the compounds of the formula (I) that possess CDK inhibitory activity. In particular the skilled reader will appreciate that when $R^4$ is hydrogen, the imidazole ring as drawn in formula (I) may tautomerise.

It is also to be understood that certain compounds of the formula (I) can exist in solvated as well as unsolvated forms such as, for example, hydrated forms. It is to be understood that the invention encompasses all such solvated forms which possess CDK inhibitory activity.

Suitable values of $R^1$, $R^2$, $R^3$, $R^4$, $R^5$ and p are as follows. Such values may be used where appropriate with any of the definitions, claims or embodiments defined hereinbefore.

$R^1$ is fluoro, chloro, cyano, methyl, ethyl, methoxy or ethoxy.

p is 0.

p is 1.

p is 2; wherein the values of $R^1$ may be the same or different.

$R^2$ is $C_{1-4}$alkyl, $C_{2-4}$alkenyl, $C_{3-6}$cycloalkyl, $C_{3-6}$cycloalkyl$C_{1-3}$alkyl or heterocyclyl$C_{1-3}$alkyl; wherein $R^2$ may be optionally substituted on carbon by one or more methyl, methoxy, ethoxy, trifluoromethyl.

$R^2$ is $C_{1-4}$alkyl, $C_{2-4}$alkenyl, $C_{3-6}$cycloalkyl, $C_{3-6}$cycloalkyl$C_{1-3}$alkyl or heterocyclyl$C_{1-3}$alkyl; wherein $R^2$ may be optionally substituted on carbon by one or more methoxy, ethoxy, trifluoromethyl.

$R_2$ is hydrogen, $C_{1-4}$alkyl, $C_{2-4}$alkenyl, $C_{3-6}$cycloalkyl, $C_{3-6}$cycloalkyl$C_{1-3}$alkyl or heterocyclyl$C_{1-3}$alkyl; wherein $R^2$ may be optionally substituted on carbon by one or more hydroxy, methoxy, ethoxy or trifluoromethyl.

$R^2$ is methyl, ethyl, propyl, t-butyl, allyl, cyclopropyl, cyclobutyl, cyclopropylmethyl or tetrahydrofur-2-ylmethyl; wherein $R^2$ may be optionally substituted on carbon by one or more methyl, methoxy, ethoxy, trifluoromethyl.

$R^2$ is methyl, ethyl, propyl, t-butyl, allyl, cyclopropyl, cyclobutyl, cyclopropylmethyl or tetrahydrofur-2-ylmethyl; wherein $R^2$ may be optionally substituted on carbon by one or more methoxy, ethoxy, trifluoromethyl.

$R^2$ is hydrogen, methyl, ethyl, propyl, t-butyl, allyl, cyclopropyl, cyclobutyl, cyclopropylmethyl or tetrahydrofur-2-ylmethyl; wherein $R^2$ may be optionally substituted on carbon by one or more hydroxy, methoxy, ethoxy, trifluoromethyl.

$R^2$ is 2-ethoxyethyl, 2-methoxyethyl, 2,2,2-trifluoroethyl, 3-methoxypropyl, t-butyl, allyl, cyclopropyl, cyclobutyl, cyclopropylmethyl or tetrahydrofur-2-ylmethyl.

$R^2$ is hydrogen, 2-ethoxyethyl, 2-methoxyethyl, 2-hydroxyethyl, 2,2,2-trifluoroethyl, 3-methoxypropyl, t-butyl, allyl, cyclopropyl, cyclobutyl, cyclopropylmethyl or tetrahydrofur-2-ylmethyl.

$R^3$ is hydrogen.

$R^4$ is $C_{1-4}$alkyl or $C_{1-4}$alkoxy$C_{1-4}$alkyl.

$R^4$ is $C_{1-6}$alkyl.

$R^4$ is $C_{1-4}$alkyl.

$R^4$ is methyl, ethyl, isopropyl or 1-methoxyprop-2-yl.

$R^4$ is methyl, ethyl, propyl, isopropyl or 1-methoxyprop-2-yl.

$R^5$ is substituted methyl or optionally substituted $C_{2-6}$alkyl; wherein said substituents are selected from one or more methoxy.

$R^5$ is substituted methyl, $C_{3-6}$cycloalkyl, optionally substituted $C_{2-6}$alkenyl or optionally substituted $C_{2-6}$alkyl; wherein said substituents are selected from one or more methoxy or hydroxy.

$R^5$ is substituted methyl, optionally substituted $C_{2-6}$alkyl, $C_{3-6}$cycloalkyl or optionally substituted $C_{2-6}$alkenyl; wherein said substituents are selected from one or more hydroxy, methoxy, ethoxy, isopropoxy, phenyl, ethylamino, dimethylamino, methylthio, ethylthio, isopropylthio, ethylsulphinyl or ethylsulphonyl.

$R^5$ is methoxymethyl, isopropyl, ethyl, butyl or 3,3-dimethylbutyl.

$R^5$ is methoxymethyl, 2-methoxyethyl, 2-hydroxy-2-methylpropyl, propyl, isopropyl, ethyl, butyl, isobutyl, cyclopropyl, 2-methyl-1-propenyl, 3-butenyl, 1-propenyl or 3,3-dimethylbutyl.

$R^5$ is methoxymethyl, 2-methoxyethyl, 2-hydroxy-2-methylpropyl, propyl, isopropyl, ethyl, butyl, isobutyl, cyclopropyl, 2-methyl-1-propenyl, 3-butenyl, 1-propenyl, 3,3-dimethylbutyl, phenethyl, dimethylaminomethyl, ethylaminomethyl, ethoxymethyl, methylthiomethyl, isopropylthiomethyl, ethylthiomethyl, ethylsulphinlmethyl, ethylsulphonylmethyl or isopropoxymethyl.

Therefore in another aspect of the invention, there is provided a compound of formula (I) (as depicted above) wherein:

p is 0;

$R^2$ is $C_{1-4}$alkyl, $C_{2-4}$alkenyl, $C_{3-6}$cycloalkyl, $C_{3-6}$cycloalkyl$C_{1-3}$alkyl or heterocyclyl$C_{1-3}$alkyl; wherein $R^2$ may be optionally substituted on carbon by one or more methoxy, ethoxy, trifluoromethyl;

$R^3$ is hydrogen;

$R^4$ is $C_{1-4}$alkyl or $C_{1-4}$alkoxy$C_{1-4}$alkyl;

$R^5$ is substituted methyl or optionally substituted $C_{2-6}$alkyl; wherein said substituents are selected from one or more methoxy;

or a pharmaceutically acceptable salt or an in vivo hydrolysable ester thereof;

provided that the compound is not 4-(1-methyl-2-ethylimidazol-5-yl)-2-{4-[N-(tetrahydrofur-2-ylmethyl)sulphamoyl]anilino}pyrimidine; 4-(1-methyl-2-ethyl-imidazol-5-yl)-2-{4-[N-(2-methoxyethyl)sulphamoyl]anilino}pyrimidine; 4-(1-methyl-2-isopropyl-imidazol-5-yl)-2-{4-[N-(2-methoxyethyl)sulphamoyl]anilino}pyrimidine; 4-(1-methyl-2-isopropyl-imidazol-5-yl)-2-{4-[N-(cyclopropylmethyl)sulphamoyl]anilino}pyrimidine; 4-(1-methyl-2-isopropyl-imidazol-5-yl)-2-{4-[N-(tetrahydrofur-2-ylmethyl)sulphamoyl]anilino}pyrimidine; 4-(1-methyl-2-ethylimidazol-5-yl)-2-{4-[N-(cyclopropylmethyl)sulphamoyl]anilino}pyrimidine; 4-(1-methyl-2-trifluoromethylimidazol-5-yl)-2-{4-[N-(tetrahydrofur-2-ylmethyl)sulphamoyl]anilino}pyrimidine; 4-(1-methyl-2-ethyl-imidazol-5-yl)-2-[4-(N-cyclopropylsulphamoyl) anilino]pyrimidine; 4-(1-methyl-2-ethylimidazol-5-yl)-2-[4-(N-cyclobutyl-sulphamoyl) anilino]pyrimidine; or 4-(1-methyl-2-methoxymethylimidazol-5-yl)-2-{4-[N-(2-methoxyethyl) sulphamoyl]anilino}pyrimidine.

Therefore in another aspect of the invention, there is provided a compound of formula (I) (as depicted above) wherein:

p is 0;

$R^2$ is $C_{1-4}$alkyl, $C_{2-4}$alkenyl, $C_{3-6}$cycloalkyl, $C_{3-6}$cycloalkyl$C_{1-3}$alkyl or heterocyclyl$C_{1-3}$alkyl; wherein $R^2$ may be optionally substituted on carbon by one or more methoxy, ethoxy, trifluoromethyl;

$R^3$ is hydrogen;

$R^4$ is $C_{1-4}$alkyl or $C_{1-4}$alkoxy$C_{1-4}$alkyl;

$R^5$ is substituted methyl, $C_{3-6}$cycloalkyl, optionally substituted $C_{2-6}$alkenyl or optionally substituted $C_{2-6}$alkyl; wherein said substituents are selected from one or more methoxy or hydroxy;

or a pharmaceutically acceptable salt or an in vivo hydrolysable ester thereof; provided that the compound is not 4-(1-methyl-2-ethylimidazol-5-yl)-2-{4-[N-(tetrahydrofur-2-ylmethyl)sulphamoyl]anilino}pyrimidine; 4-(1-methyl-2-ethyl-imidazol-5-yl)-2-{4-[N-(2-methoxyethyl)sulphamoyl] anilino}pyrimidine; 4-(1-methyl-2-isopropyl-imidazol-5-yl)-2-{4-[N-(2-methoxyethyl)sulphamoyl] anilino}pyrimidine; 4-(1-methyl-2-isopropyl-imidazol-5-yl)-2-{4[N-(cyclopropylmethyl)sulphamoyl] anilino}pyrimidine; 4-(1-methyl-2-isopropyl-imidazol-5-yl)-2-{4-[N-(tetrahydrofur-2-ylmethyl)sulphamoyl] anilino}pyrimidine; 4-(1-methyl-2-ethylimidazol-5-yl)-2-{4-[N-(cyclopropylmethyl)sulphamoyl]anilino}pyrimidine; 4-(1-methyl-2-trifluoromethylimidazol-5-yl)-2-{4-[N-(tetrahydrofur-2-ylmethyl)sulphamoyl]anilino}pyrimidine; 4-(1-methyl-2-ethyl-imidazol-5-yl)-2-[4-(N-cyclopropyl-sulphamoyl) anilino]pyrimidine; 4-(1-methyl-2-ethylimidazol-5-yl)-2-[4-(N-cyclobutyl-sulphamoyl) anilino]pyrimidine; or 4-(1-methyl-2-methoxymethylimidazol-5-yl)-2-{4-[N-(2-methoxyethyl) sulphamoyl]anilino}pyrimidine.

Therefore in another aspect of the invention, there is provided a compound of formula (I) (as depicted above) wherein:

p is 0;

$R^2$ is hydrogen, $C_{1-4}$alkyl, $C_{2-4}$alkenyl, $C_{3-6}$cycloalkyl, $C_{3-6}$cycloalkyl$C_{1-3}$alkyl or heterocyclyl$C_{1-3}$alkyl; wherein $R^2$ may be optionally substituted on carbon by one or more hydroxy, methoxy, ethoxy or trifluoromethyl;

$R^3$ is hydrogen;

$R^4$ is $C_{1-4}$alkyl or $C_{1-4}$alkoxy$C_{1-4}$alkyl; or $R^5$ is substituted methyl, optionally substituted $C_2$ alkyl, $C_{3-6}$cycloalkyl or optionally substituted $C_{2-6}$alkenyl; wherein said substituents are selected from one or more hydroxy, methoxy, ethoxy, isopropoxy, phenyl, ethylamino, dimethylamino, methylthio, ethylthio, isopropylthio, ethylsulphinyl or ethylsulphonyl;

or a pharmaceutically acceptable salt or an in vivo hydrolysable ester thereof; provided that the compound is not 4-(1-methyl-2-ethylimidazol-5-yl)-2-{4-[N-(tetrahydrofur-2-ylmethyl)sulphamoyl]anilino}pyrimidine; 4-(1-methyl-2-ethyl-imidazol-5-yl)-2-{4-[N-(2-methoxyethyl)sulphamoyl] anilino}pyrimidine; 4-(1-methyl-2-isopropyl-imidazol-5-yl)-2-{4-[N-(2-methoxyethyl)sulphamoyl] anilino}pyrimidine; 4-(1-methyl-2-isopropyl-imidazol-5-yl)-2-{4-[N-(cyclopropylmethyl)sulphamoyl] anilino}pyrimidine; 4-(1-methyl-2-isopropyl-imidazol-5-yl)-2-{4-[N-(tetrahydrofur-2-ylmethyl)sulphamoyl] anilino}pyrimidine; 4-(1-methyl-2-ethylimidazol-5-yl)-2-{4-[N-(cyclopropylmethyl)sulphamoyl]anilino}pyrimidine; 4-(1-methyl-2-ethyl-imidazol-5-yl)-2-[4-(N-cyclopropyl-sulphamoyl)anilino]pyrimidine; 4-(1-methyl-2-ethylimidazol-5-yl)-2-[4-(N-cyclobutyl-sulphamoyl)anilino]pyrimidine; or 4-(1-methyl-2-methoxymethylimidazol-5-yl)-2-{4-[N-(2-methoxyethyl) sulphamoyl]anilino}pyrimidine.

Therefore in an additional aspect of the invention, there is provided a compound of formula (I) (as depicted above) wherein:

p is 0;

$R^2$ is 2-ethoxyethyl, 2-methoxyethyl, 2,2,2-trifluoroethyl, 3-methoxypropyl, t-butyl, allyl, cyclopropyl, cyclobutyl, cyclopropylmethyl or tetrahydrofur-2-ylmethyl;

$R^3$ is hydrogen;

$R^4$ is methyl, ethyl, isopropyl or 1-methoxyprop-2-yl;

$R^5$ is methoxymethyl, isopropyl, ethyl, butyl or 3,3-dimethylbutyl;

or a pharmaceutically acceptable salt or an in vivo hydrolysable ester thereof; provided that the compound is not 4-(1-methyl-2-ethylimidazol-5-yl)-2-{4-[N-(tetrahydrofur-2-ylmethyl)sulphamoyl]anilino}pyrimidine; 4-(1-methyl-2-ethyl-imidazol-5-yl)-2-{4-[N-(2-methoxyethyl)sulphamoyl] anilino}pyrimidine; 4-(1-methyl-2-isopropyl-imidazol-5-yl)-2-{4-[N-(2-methoxyethyl)sulphamoyl] anilino}pyrimidine; 4-(1-methyl-2-isopropyl-imidazol-5-yl)-2-{4-[N-(cyclopropylmethyl)sulphamoyl] anilino}pyrimidine; 4-(1-methyl-2-isopropyl-imidazol-5-yl)-2-{4-[N-(tetrahydrofur-2-ylmethyl)sulphamoyl] anilino}pyrimidine; 4-(1-methyl-2-ethylimidazol-5-yl)-2-{4-[N-(cyclopropylmethyl)sulphamoyl]anilino}pyrimidine; 4-(1-methyl-2-trifluoromethylimidazol-5-yl)-2-{4-[N-(tetrahydrofur-2-ylmethyl)sulphamoyl]anilino}pyrimidine; 4-(1-methyl-2-ethyl-imidazol-5-yl)-2-[4-(N-cyclopropyl-sulphamoyl) anilino]pyrimidine; 4-(1-methyl-2-ethylimidazol-5-yl)-2-[4-(N-cyclobutyl-sulphamoyl) anilino]pyrimidine; or 4-(1-methyl-2-methoxymethylimidazol-5-yl)-2-{4-[N-(2-methoxyethyl) sulphamoyl]anilino}pyrimidine.

Therefore in an additional aspect of the invention, there is provided a compound of formula (I) (as depicted above) wherein:

p is 0;

$R^2$ is 2-ethoxyethyl, 2-methoxyethyl, 2,2,2-trifluoroethyl, 3-methoxypropyl, t-butyl, allyl, cyclopropyl, cyclobutyl, cyclopropylmethyl or tetrahydrofur-2-ylmethyl;

$R^3$ is hydrogen;

$R^4$ is methyl, ethyl, propyl, isopropyl or 1-methoxyprop-2-yl;

$R^5$ is methoxymethyl, 2-methoxyethyl, 2-hydroxy-2-methylpropyl, propyl, isopropyl, ethyl, butyl, isobutyl, cyclopropyl, 2-methyl-1-propenyl, 3-butenyl, 1-propenyl or 3,3-dimethylbutyl;

or a pharmaceutically acceptable salt or an in vivo hydrolysable ester thereof; provided that the compound is not 4-(1-methyl-2-ethylimidazol-5-yl)-2-{4-[N-(tetrahydrofur-2-ylmethyl)sulphamoyl]anilino}pyrimidine; 4-(1-methyl-2-ethyl-imidazol-5-yl)-2-{4-[N-(2-methoxyethyl)sulphamoyl] anilino}pyrimidine; 4-(1-methyl-2-isopropyl-imidazol-5-yl)-2-{4-[N-(2-methoxyethyl)sulphamoyl] anilino}pyrimidine; 4-(1-methyl-2-isopropyl-imidazol-5-yl)-2-{4-[N-(cyclopropylmethyl)sulphamoyl] anilino}pyrimidine; 4-(1-methyl-2-isopropyl-imidazol-5-yl)-2-{4-[N-(tetrahydrofur-2-ylmethyl)sulphamoyl] anilino}pyrimidine; 4-(1-methyl-2-ethylimidazol-5-yl)-2-{4-[N-(cyclopropylmethyl)sulphamoyl]anilino}pyrimidine; 4-(1-methyl-2-trifluoromethylimidazol-5-yl)-2-{4-[N-(tetrahydrofur-2-ylmethyl)sulphamoyl]anilino}pyrimidine; 4-(1-methyl-2-ethyl-imidazol-5-yl)-2-[4-(N-cyclopropyl-sulphamoyl) anilino]pyrimidine; 4-(1-methyl-2-ethylimidazol-5-yl)-2-[4-(N-cyclobutyl-sulphamoyl) anilino]pyrimidine; or 4-(1-methyl-2-methoxymethylimidazol-5-yl)-2-{4-[N-(2-methoxyethyl) sulphamoyl]anilino}pyrimidine.

Therefore in an additional aspect of the invention, there is provided a compound of formula (I) (as depicted above) wherein:

p is 0;

$R^2$ is hydrogen, 2-ethoxyethyl, 2-methoxyethyl, 2-hydroxyethyl, 2,2,2-trifluoroethyl, 3-methoxypropyl, t-butyl, allyl, cyclopropyl, cyclobutyl, cyclopropylmethyl or tetrahydrofur-2-ylmethyl;

$R^3$ is hydrogen;

$R^4$ is methyl, ethyl, propyl, isopropyl or 1-methoxyprop-2-yl; or $R^5$ is methoxymethyl, 2-methoxyethyl, 2-hydroxy-2-methylpropyl, propyl, isopropyl, ethyl, butyl, isobutyl, cyclopropyl, 2-methyl-1-propenyl, 3-butenyl, 1-propenyl, 3,3-dimethylbutyl, phenethyl, dimethylaminomethyl, ethylaminomethyl, ethoxymethyl, methylthiomethyl, isopropylthiomethyl, ethylthiomethyl, ethylsulphinlmethyl, ethylsulphonylmethyl or isopropoxymethyl;

or a pharmaceutically acceptable salt or an in vivo hydrolysable ester thereof; provided that the compound is not 4-(1-methyl-2-ethylimidazol-5-yl)-2-{4-[N-(tetrahydrofur-2-ylmethyl)sulphamoyl]anilino}pyrimidine; 4-(1-methyl-2-ethyl-imidazol-5-yl)-2-{4-[N-(2-methoxyethyl)sulphamoyl]anilino}pyrimidine; 4-(1-methyl-2-isopropyl-imidazol-5-yl)-2-{4-[N-(2-methoxyethyl)sulphamoyl]anilino}pyrimidine; 4-(1-methyl-2-isopropyl-imidazol-5-yl)-2-{4-[N-(cyclopropylmethyl)sulphamoyl]anilino}pyrimidine; 4-(1-methyl-2-isopropyl-imidazol-5-yl)-2-{4-[N-(tetrahydrofur-2-ylmethyl)sulphamoyl]anilino}pyrimidine; 4-(1-methyl-2-ethylimidazol-5-yl)-2-{4-[N-(cyclopropylmethyl)sulphamoyl]anilino}pyrimidine; 4-(1-methyl-2-ethyl-imidazol-5-yl)-2-[4-(N-cyclopropyl-sulphamoyl)anilino]pyrimidine; 4-(1-methyl-2-ethylimidazol-5-yl)-2-[4-(N-cyclobutyl-sulphamoyl)anilino]pyrimidine; or 4-(1-methyl-2-methoxymethylimidazol-5-yl)-2-{4-[N-(2-methoxyethyl)sulphamoyl]anilino}pyrimidine.

In another aspect of the invention, particular compounds of the invention are any one of the Examples or a pharmaceutically acceptable salt or an in vivo hydrolysable ester thereof.

In another aspect of the invention, particular compounds of the invention are one of Examples 4, 12, 30, 31, 44, 51, 54, 58, 60 or 61 or a pharmaceutically acceptable salt or an in vivo hydrolysable ester thereof.

A particular aspect of the invention is that which relates to the compound of formula (I) or a pharmaceutically acceptable salt thereof.

Another aspect of the present invention provides a process for preparing a compound of formula (I) or a pharmaceutically acceptable salt or an in vivo hydrolysable ester thereof which process (wherein $R^1$, $R^2$, $R^3$, $R^4$, $R^5$ and p are, unless otherwise specified, as defined in formula (I)) comprises of:

Process a) reaction of a pyrimidine of formula (II):

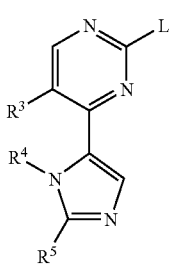

(II)

wherein L is a displaceable group; with an aniline of formula (III):

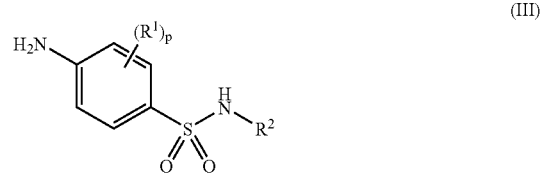

(III)

Process b) reacting a compound of formula (IV):

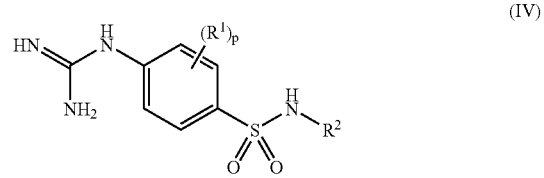

(IV)

with a compound of formula (V):

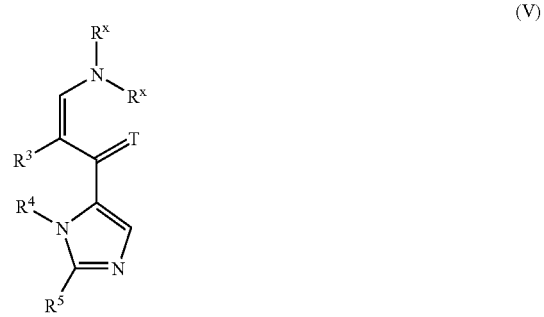

(V)

wherein T is O or S; $R^x$ may be the same or different and is $C_{1-6}$alkyl;

Process c) reacting a pyrimidine of formula (VI):

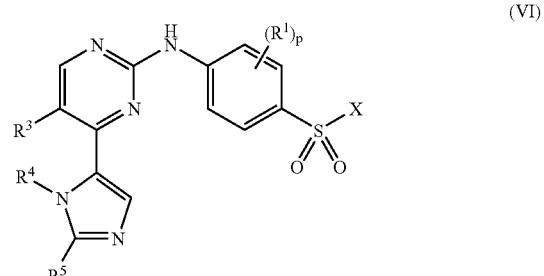

(VI)

wherein X is a displaceable group; with an amine of formula (VII):

$R^2$—$NH_2$  (VII)

or

Process d) reacting a pyrimidine of formula (VIII)

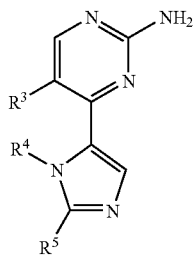
(VIII)

with a compound of formula (IX):

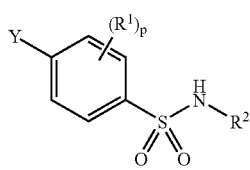
(IX)

where Y is a displaceable group;
and thereafter if necessary:
i) converting a compound of the formula (I) into another compound of the formula (I);
ii) removing any protecting groups;
iii) forming a pharmaceutically acceptable salt or in vivo hydrolysable ester.

L is a displaceable group, suitable values for L are for example, a halogeno or sulphonyloxy group, for example a chloro, bromo, methanesulphonyloxy or toluene-4-sulphonyloxy group.

X is a displaceable group, suitable values for X are for example, a fluoro or chloro group. Preferably X is fluoro.

Y is a displaceable group, suitable values for Y are for example, a halogeno or sulphonyloxy group, for example a bromo, iodo or trifluoromethanesulphonyloxy group. Preferably Y is iodo.

Specific reaction conditions for the above reactions are as follows.

Process a) Pyrimidines of formula (II) and anilines of formula (III) may be reacted together:
i) in the presence of a suitable solvent for example a ketone such as acetone or an alcohol such as ethanol or butanol or an aromatic hydrocarbon such as toluene or N-methyl pyrrolidine, optionally in the presence of a suitable acid for example an inorganic acid such as hydrochloric acid or sulphuric acid, or an organic acid such as acetic acid or formic acid (or a suitable Lewis acid) and at a temperature in the range of 0° C. to reflux, preferably reflux; or
ii) under standard Buchwald conditions (for example see *J. Am. Chem. Soc.*, 118, 7215; *J. Am. Chem. Soc.*, 119, 8451; *J. Org. Chem.*, 62, 1568 and 6066) for example in the presence of palladium acetate, in a suitable solvent for example an aromatic solvent such as toluene, benzene or xylene, with a suitable base for example an inorganic base such as caesium carbonate or an organic base such as potassium-t-butoxide, in the presence of a suitable ligand such as 2,2'-bis(diphenylphosphino)-1,1'-binaphthyl and at a temperature in the range of 25 to 80° C.

Pyrimidines of the formula (II) where L is chloro may be prepared according to Scheme 1:

Scheme 1

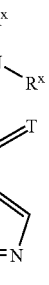 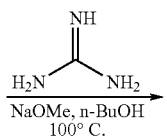

(V)

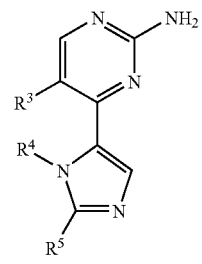
(VIII)

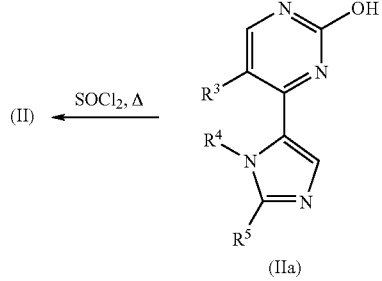
(IIa)

Anilines of formula (III) are commercially available compounds, or they are known in the literature, or they are prepared by standard processes known in the art.

Process b) Compounds of formula (IV) and compounds of formula (V) are reacted together in a suitable solvent such as N-methylpyrrolidinone or butanol at a temperature in the range of 100-200° C., preferably in the range of 150-170° C. The reaction is preferably conducted in the presence of a suitable base such as, for example, sodium hydride, sodium methoxide or potassium carbonate.

Compounds of formula (V) may be prepared according to Scheme 2:

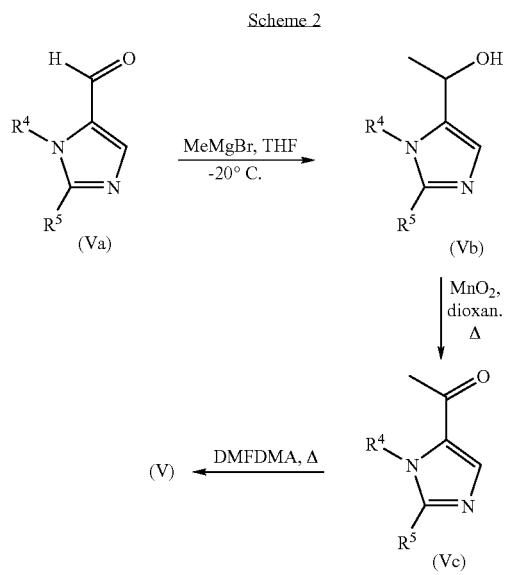

Compounds of formula (IV) and (Va) are commercially available compounds, or they are known in the literature, or they are prepared by standard processes known in the art.

Process c) Compounds of formula (VI) and amines of formula (VII) may be reacted together in the presence of an inert solvent such as N-methylpyrrolidinone or pyridine, in the presence of a base for example an inorganic base such as caesium carbonate or in the presence of an organic base such as excess (VII) and at a temperature in the range of 25 to 80° C.

Compounds of formula (VI) (wherein X is chloro) may be prepared according to Scheme 3:

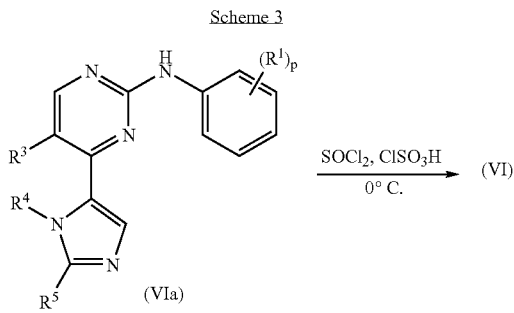

Compounds of formula (VIa) may be prepared according to Process a, Process b or Process d but wherein compounds (III), (IV) and (IX) are not substituted by $R^2NHSO_2$—.

Process d) Compounds of formula (VIII) and amines of formula (IX) may be reacted together under standard Buchwald conditions as described in Process a.

The synthesis of compounds of formula (VIII) is described in Scheme 1.

Compounds of formula (IX) are commercially available compounds, or they are known in the literature, or they are prepared by standard processes known in the art.

Amines of formula (VI) are commercially available compounds, or they are known in the literature, or they are prepared by standard processes known in the art.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

As stated hereinbefore the compounds defined in the present invention possesses anti-cell-proliferation activity such as anti-cancer activity which is believed to arise from the CDK inhibitory activity of the compound. These properties may be assessed, for example, using the procedures set out in WO 02/04429.

Although the pharmacological properties of the compounds of the formula (I) vary with structural change, in general activity possessed by compounds of the formula (I) may be demonstrated at $IC_{50}$ concentrations or doses in the range 250 µM to 1 nM in the in vitro assay described in WO 02/04429.

Typical $IC_{50}$ values for compounds of the invention when tested in the SRB assay described in WO 02/04429 are in the range 1 mM to 1 nM.

According to a further aspect of the invention there is provided a pharmaceutical composition which comprises a pyrimidine derivative of the formula (I), or a pharmaceutically acceptable salt or in vivo hydrolysable ester thereof, as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound of formula (I) will normally be administered to a warm-blooded animal at a unit dose within the range 5-5000 mg per square meter body area of the animal, i.e. approximately 0.1-100 mg/kg, and this normally provides a therapeutically-effective dose. A unit dose form such as a tablet or capsule will usually contain, for example 1-250 mg of active ingredient. Preferably a daily dose in the range of 1-50 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a compound of the formula (I), or a pharmaceutically acceptable salt or in vivo hydrolysable ester thereof, as defined hereinbefore for use in a method of treatment of the human or animal body by therapy.

We have found that the compounds defined in the present invention, or a pharmaceutically acceptable salt or in vivo hydrolysable ester thereof, are effective cell cycle inhibitors (anti-cell proliferation agents), which property is believed to arise from their CDK inhibitory properties. Accordingly the compounds of the present invention are expected to be useful in the treatment of diseases or medical conditions mediated alone or in part by CDK enzymes, i.e. the compounds may be used to produce a CDK inhibitory effect in a warm-blooded animal in need of such treatment. Thus the compounds of the present invention provide a method for treating the proliferation of malignant cells characterised by inhibition of CDK enzymes, i.e. the compounds may be used to produce an anti-proliferative effect mediated alone or in part by the inhibition of CDKs. Such a compound of the invention is expected to possess a wide range of anti-cancer properties as CDKs have been implicated in many common human cancers such as leukaemia and breast, lung, colon, rectal, stomach, prostate, bladder, pancreas and ovarian cancer. Thus it is expected that a compound of the invention will possess anti-cancer activity against these cancers. It is in addition expected that a compound of the present invention will possess activity against a range of leukaemias, lymphoid malignancies and solid tumours such as carcinomas and sarcomas in tissues such as the liver, kidney, prostate and pancreas. In particular such compounds of the invention are expected to slow advantageously the growth of primary and recurrent solid tumours of, for example, the colon, breast, prostate, lungs and skin. More particularly such compounds of the invention, or a pharmaceutically acceptable salt or in vivo hydrolysable ester thereof, are expected to inhibit the growth of those primary and recurrent solid tumours which are associated with CDKs, especially those tumours which are significantly dependent on CDKs for their growth and spread, including for example, certain tumours of the colon, breast, prostate, lung, vulva and skin. Particularly "cancer" is selected from leukaemia, breast cancer, lung cancer, colorectal cancer, stomach cancer, prostate cancer, bladder cancer, pancreatic cancer, ovarian cancer, liver cancer, kidney cancer, skin cancer and cancer of the vulva.

It is further expected that a compound of the present invention will possess activity against other cell-proliferation diseases in a wide range of other disease states including leukaemias, fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Thus according to this aspect of the invention there is provided a compound of the formula (I), or a pharmaceutically acceptable salt or in vivo hydrolysable ester thereof, as defined hereinbefore for use as a medicament; and the use of a compound of the formula (I), or a pharmaceutically acceptable salt or in vivo hydrolysable ester thereof, as defined hereinbefore in the manufacture of a medicament for use in the production of a cell cycle inhibitory (anti-cell-proliferation) effect in a warm-blooded animal such as man. Particularly, an inhibitory effect is produced by preventing entry into or progression through the S phase by inhibition of CDK2, CDK4 and/or CDK6, especially CDK2.

According to a further feature of the invention, there is provided a compound of the formula (I), or a pharmaceutically acceptable salt or in vivo hydrolysable ester thereof, as defined herein before in the manufacture of a medicament for use in the treatment of cancers (solid tumours and leukaemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation, particularly in the treatment of cancers.

According to a further feature of this aspect of the invention there is provided a method for producing a cell cycle inhibitory (anti-cell-proliferation) effect in a warm-blooded animal, such as man, in need of such treatment which comprises administering to said animal an effective amount of a compound as defined immediately above. Particularly, an inhibitory effect is produced by preventing entry into or progression through the S phase by inhibition of CDK2, CDK4 and/or CDK6, especially CDK2.

According to a further feature of this aspect of the invention there is provided a method for producing a cell cycle inhibitory (anti-cell-proliferation) effect in a warm-blooded animal, such as man, in need of such treatment which comprises administering to said animal an effective amount of a compound of formula (I) or a pharmaceutically acceptable salt or in vivo hydrolysable ester thereof as defined herein before. Particularly, an inhibitory effect is produced by preventing entry into or progression through the S phase by inhibition of CDK2, CDK4 and/or CDK6, especially CDK2.

According to an additional feature of this aspect of the invention there is provided a method of treating cancers (solid tumours and leukaemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation, in a warm-blooded animal, such as man, in need of such treatment which comprises administering to said animal an effective amount of a compound of formula (I) or a pharmaceutically acceptable salt or in vivo hydrolysable ester thereof as defined herein before.

Particularly there is provided a method of treating cancer in a warm-blooded animal, such as man, in need of such treatment which comprises administering to said animal an effective amount of a compound of formula (I) or a pharmaceutically acceptable salt or in vivo hydrolysable ester thereof as defined herein before.

In a further aspect of the invention there is provided a pharmaceutical composition which comprises a compound of the formula (I), or a pharmaceutically acceptable salt or in vivo hydrolysable ester thereof, as defined herein before in association with a pharmaceutically-acceptable diluent or carrier for use in the production of a cell cycle inhibitory (anti-cell-proliferation) effect in a warm-blooded animal such as man.

In a further aspect of the invention there is provided a pharmaceutical composition which comprises a compound of the formula (I), or a pharmaceutically acceptable salt or in vivo hydrolysable ester thereof, as defined herein before in association with a pharmaceutically-acceptable diluent or carrier for use in the treatment of cancers (solid tumours and leukaemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation, in a warm-blooded animal such as man.

In a further aspect of the invention there is provided a pharmaceutical composition which comprises a compound of the formula (I), or a pharmaceutically acceptable salt or in vivo hydrolysable ester thereof, as defined herein before in association with a pharmaceutically-acceptable diluent or carrier for use in the treatment of cancer in a warm-blooded animal such as man.

Preventing cells from entering DNA synthesis by inhibition of essential S-phase initiating activities such as CDK2 initiation may also be useful in protecting normal cells of the body from toxicity of cycle-specific pharmaceutical agents. Inhibition of CDK2 or 4 will prevent progression into the cell cycle in normal cells which could limit the toxicity of cycle-specific pharmaceutical agents which act in S-phase, G2 or mitosis. Such protection may result in the prevention of hair loss normally associated with these agents.

Therefore in a further aspect of the invention there is provided a compound of formula (I) as defined above or a pharmaceutically acceptable salt or in vivo hydrolysable ester thereof for use as a cell protective agent.

Therefore in a further aspect of the invention there is provided a compound of formula (I) as defined above or a pharmaceutically acceptable salt or in vivo hydrolysable ester thereof for use in preventing hair loss arising from the treatment of malignant conditions with pharmaceutical agents.

Examples of pharmaceutical agents for treating malignant conditions that are known to cause hair loss include alkylating agents such as ifosfamide and cyclophosphamide; antimetabolites such as methotrexate, 5-fluorouracil, gemcitabine and cytarabine; vinca alkaloids and analogues such as vincristine, vinbalstine, vindesine, vinorelbine; taxanes such as paclitaxel and docetaxel; topoisomerase I inhibitors such as irintotecan and topotecan; cytotoxic antibiotics such as doxorubicin, daunorubicin, mitoxantrone, actinomycin-D and mitomycin; and others such as etoposide and tretinoin.

In another aspect of the invention, the compound of formula (I), or a pharmaceutically acceptable salt or in vivo hydrolysable ester thereof, may be administered in association with a one or more of the above pharmaceutical agents. In this instance the compound of formula (I) may be administered by systemic or non systemic means. Particularly the compound of formula (I) my may administered by non-systemic means, for example topical administration.

Therefore in an additional feature of the invention, there is provided a method of preventing hair loss during treatment for one or more malignant conditions with pharmaceutical agents, in a warm-blooded animal, such as man, which comprises administering to said animal an effective amount of a compound of formula (I), or a pharmaceutically acceptable salt or in vivo hydrolysable ester thereof.

In an additional feature of the invention, there is provided a method of preventing hair loss during treatment for one or more malignant conditions with pharmaceutical agents, in a warm-blooded animal, such as man, which comprises administering to said animal an effective amount of a compound of formula (I), or a pharmaceutically acceptable salt or in vivo hydrolysable ester thereof in simultaneous, sequential or separate administration with an effective amount of said pharmaceutical agent.

According to a further aspect of the invention there is provided a pharmaceutical composition for use in preventing hair loss arising from the treatment of malignant conditions with pharmaceutical agents which comprises a compound of formula (I), or a pharmaceutically acceptable salt or in vivo hydrolysable ester thereof, and said pharmaceutical agent, in association with a pharmaceutically acceptable diluent or carrier.

According to a further aspect of the present invention there is provided a kit comprising a compound of formula (I), or a pharmaceutically acceptable salt or in vivo hydrolysable ester thereof, and a pharmaceutical agent for treating malignant conditions that is known to cause hair loss.

According to a further aspect of the present invention there is provided a kit comprising:

a) a compound of formula (I), or a pharmaceutically acceptable salt or in vivo hydrolysable ester thereof, in a first unit dosage form;
b) a pharmaceutical agent for treating malignant conditions that is known to cause hair loss; in a second unit dosage form; and
c) container means for containing said first and second dosage forms.

According to another feature of the invention there is provided the use of a compound of the formula (I), or a pharmaceutically acceptable salt or in vivo hydrolysable ester thereof, in the manufacture of a medicament for the prevention of hair loss during treatment of malignant conditions with pharmaceutical agents.

According to a further aspect of the present invention there is provided a combination treatment for the prevention of hair loss comprising the administration of an effective amount of a compound of the formula (I), or a pharmaceutically acceptable salt or in vivo hydrolysable ester thereof, optionally together with a pharmaceutically acceptable diluent or carrier, with the simultaneous, sequential or separate administration of an effective amount of a pharmaceutical agent for treatment of malignant conditions to a warm-blooded animal, such as man.

As stated above the size of the dose required for the therapeutic or prophylactic treatment of a particular cell-proliferation disease will necessarily be varied depending on the host treated, the route of administration and the severity of the illness being treated. A unit dose in the range, for example, 1-100 mg/kg, preferably 1-50 mg/kg is envisaged.

The CDK inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the cell cycle inhibitory treatment defined hereinbefore may be: surgery, radiotherapy or chemotherapy. Such chemotherapy may cover three main categories of therapeutic agent:

(i) other cell cycle inhibitory agents that work by the same or different mechanisms from those defined hereinbefore;
(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincristine and taxoids like taxol, taxotere); topoisomerase inhibitors (for example epipodophyllotoxins like etoposide and teniposide, amsacrine, topotecan). According to this aspect of the invention there is provided a pharmaceutical product comprising a compound of the formula (I) as defined hereinbefore and an additional anti-tumour substance as defined hereinbefore for the conjoint treatment of cancer.

In addition to their use in therapeutic medicine, the compounds of formula (I) and their pharmaceutically acceptable salts are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

In the above other pharmaceutical composition, process, method, use and medicament manufacture features, the alternative and preferred embodiments of the compounds of the invention described herein also apply.

EXAMPLES

The invention will now be illustrated by the following non limiting examples in which, unless stated otherwise:

(i) temperatures are given in degrees Celsius (° C.); operations were carried out at room or ambient temperature, that is, at a temperature in the range of 18-25° C.;
(ii) organic solutions were dried over anhydrous magnesium sulphate; evaporation of solvent was carried out using a rotary evaporator under reduced pressure (600-4000 Pascals; 4.5-30 mmHg) with a bath temperature of up to 60° C.;
(iii) chromatography means flash chromatography on silica gel; thin layer chromatography (TLC) was carried out on silica gel plates;
(iv) in general, the course of reactions was followed by TLC and reaction times are given for illustration only;
(v) final products had satisfactory proton nuclear magnetic resonance (NMR) spectra and/or mass spectral data;
(vi) yields are given for illustration only and are not necessarily those which can be obtained by diligent process development; preparations were repeated if more material was required;
(vii) when given, NMR data is in the form of delta values for major diagnostic protons, given in parts per million (ppm) relative to tetramethylsilane (TMS) as an internal standard, determined at 300 MHz using perdeuterio dimethyl sulphoxide (DMSO-$d_6$) as solvent unless otherwise indicated; and peak multiplicities are shown as follows: s, singlet; d, doublet; dd, double doublet; t, triplet; tt, triple triplet; q, quartet; tq, triple quartet; m, multiplet; br, broad;
(viii) chemical symbols have their usual meanings; SI units and symbols are used;
(ix) solvent ratios are given in volume:volume (v/v) terms; and (x) mass spectra were run with an electron energy of 70 electron volts in the chemical ionization (CI) mode using a direct exposure probe; where indicated ionization was effected by electron impact (EI), fast atom bombardment (FAB) or electrospray (ESP); values for m/z are given; generally, only ions which indicate the parent mass are reported; and unless otherwise stated, the mass ion quoted is (MH)$^+$;

(xi) unless stated otherwise compounds containing an asymmetrically substituted carbon and/or sulphur atom have not been resolved;

(xii) where a synthesis is described as being analogous to that described in a previous example the amounts used are the millimolar ratio equivalents to those used in the previous example;

(xvi) the following abbreviations have been used:

| | |
|---|---|
| DMF | dimethylformamide; |
| EtOAc | ethyl acetate; |
| ether | diethyl ether; |
| MeOH | methanol; and |
| DCM | dichloromethane; | xvii) where an Isolute SCX-2 column is referred to, this means an "ion exchange" extraction cartridge for adsorption of basic compounds, i.e. a polypropylene tube containing a benzenesulphonic acid based strong cation exchange sorbent, used according to the manufacturers instructions obtained from International Sorbent Technologies Limited, Dyffryn Business Park, Hengeod, Mid Glamorgan, UK, CF82 7RJ;

xviii) where an Isolute amine column is referred to, this means an "ion exchange" extraction cartridge for adsorption of acidic compounds, i.e. a polypropylene tube containing a amino silane covalently bonded to a silica particle used according to the manufacturers instructions obtained from International Sorbent Technologies Limited, Dyffryn Business Park, Hengeod, Mid Glamorgan, UK, CF82 7RJ; and xix) where a Chemelut column is referred to, this means an extraction cartridge for removal of water, i.e. a polypropylene tube containing diatomaceous earth used according to the manufacturers instructions obtained from Varian, Harbor City, Calif., USA.

Example 1

4-(1-Methyl-2-isopropylimidazol-5-yl)-2-{4-[N-(cyclobutyl)sulphamoyl]anilino}pyrimidine Chlorosulphonic acid (150 µl, 2.16 mmol) was added dropwise to solution of 2-anilino-4-(1-methyl-2-isopropylimidazol-5-yl)pyrimidine (Method 71; 158 mg, 0.54 mmol) in thionyl chloride (3 ml) cooled at 0° C. and the mixture stirred at 0° C. for 10 minutes then heated at 90° C. for 90 minutes. The volatiles were removed by evaporation and the residue was dried under high vacuum (<2 mmHg) for 1 hour. The resulting solid was placed under nitrogen and a solution of cyclobutylamine (100 µl, 1.08 mmol) and diethylmethylamine (1 ml, 15 mmol) in MeOH (3 ml) added. The mixture was stirred for 30 minutes and the volatiles were evaporated in vacuo. Trituration with water results in a solid which was washed water (3×20 ml) collected by filtration and dried under vacuum at 60° C. to yield the title compound (151 mg, 65%) as a solid. NMR: 1.24 (d, 6H), 1.45 (m, 2H), 1.70 (m, 2H), 1.90 (m, 2H), 3.17 (m, 1H), 3.58 (m, 1H), 3.98 (s, 3H), 7.19 (d, 1H), 7.70 (m, 4H), 7.92 (d, 2H), 8.41 (d, 1H), 9.90 (brs, 1H); m/z 427.

Examples 2-23

The following compounds were prepared by the procedure of Example 1 using the appropriate starting materials.

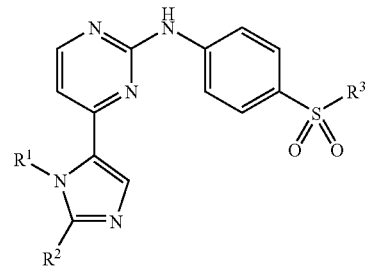

| Ex | R$^1$ | R$^2$ | R$^3$ | NMR | M/z | SM |
|---|---|---|---|---|---|---|
| 2$^{1,3}$ | Et | Et | ![NH-tetrahydrofuranylmethyl] | 1.25(t, 3H), 1.36(t, 3H), 1.51(m, 1H), 1.78(m, 3H), 2.75(s, 2H), 3.08(q, 2H), 3.55(m, 1H), 3.65 (m, 1H), 3.74(quin, 1H), 4.76(q, 2H), 7.39(d, 1H), 7.55(br t, 1H), 7.72(d, 2H), 7.88(d, 2H), 8.49(s, 1H), 8.65(d, 1H), 10.16(s, 1H) | 457 | Meth 73 |
| 3$^{1,3}$ | Et | Et | ![NH-CH2CH2-O-CH3] | 1.25(t, 3H), 1.36(t, 3H), 2.87(s, 2H), 3.08(q, 2H), 3.16(s, 3H), 3.29(t, 2H), 4.76(q, 2H), 7.40(d, 1H), 7.55(brs, 1H), 7.73(d, 2H), 7.88(d, 2H), 8.51(s, 1H), 8.65(d, 1H), 10.16(s, 1H) | 431 | Meth 73 |

-continued

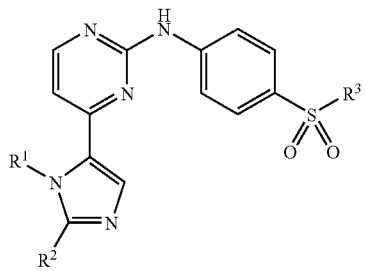

| Ex | R¹ | R² | R³ | NMR | M/z | SM |
|---|---|---|---|---|---|---|
| 4[1,3] | Et | Et | NH-CH2CH2-O-CH2CH3 | 1.04(t, 3H), 1.25(t, 3H), 1.36(t, 3H), 2.88(q, 2H), 3.09(q, 2H), 3.34(m, 4H), 4.76(q, 2H), 7.40(d, 1H), 7.53(t, 1H), 7.72(d, 2H), 7.88(d, 2H), 8.49(s, 1H), 8.65(d, 1H), 10.16(s, 1H) | 445 | Meth 73 |
| 5[1,3] | Et | Et | NH-CH2CH2CH2-O-CH3 | 1.26(t, 3H), 1.37(t, 3H), 1.59 (quintet, 2H), 2.76(m, 2H), 3.08 (m, 2H), 3.15(s, 3H), 3.27(t, 2H), 4.76(q, 2H), 7.40(m, 2H), 7.71(d, 2H), 7.89(d, 2H), 8.49(s, 1H), 8.67(d, 1H), 10.16(s, 1H) | 445 | Meth 73 |
| 6[1,4] | Et | MeOCH2— | NH-CH2-(tetrahydrofuran-2-yl) | 1.30(t, 3H), 1.55(m, 1H), 1.77(m, 2H), 1.87(m, 1H), 2.79(m, 2H), 3.45(s, 3H), 3.60(m, 1H), 3.71(m, 1H), 3.83(m, 1H), 4.77(q, 2H), 4.87(s, 2H), 7.42(d, 1H), 7.57(t, 1H), 7.78(d, 2H), 7.90(d, 2H), 8.45(s, 1H), 8.67(d, 1H), 10.12(s, 1H) | 473 | Meth 72 |
| 7[1,4] | Et | MeOCH2— | NH-CH2CH2-O-CH2CH3 | 1.05(t, 3H), 1.28(t, 3H), 2.88(m, 2H), 3.35(q, 4H), 3.43(s, 3H), 4.77(q, 2H), 4.88(s, 2H), 7.40(d, 1H), 7.52(brs, 1H), 7.73(d, 2H), 7.88(d, 2H), 8.53(s, 1H), 8.68(d, 1H), 10.16(s, 1H) | 461 | Meth 72 |
| 8[1,4] | Et | MeOCH2— | NH-CH2CH2CH2-O-CH3 | 1.27(t, 3H), 1.59(quintet, 2H), 2.78(q, 2H), 3.16(s, 3H), 3.28(t, 2H), 3.42(s, 3H), 4.75(q, 2H), 4.84(s, 2H), 7.41(m, 2H), 7.73(d, 2H), 7.89(d, 2H), 8.44(s, 1H), 8.67(d, 1H), 10.10(s, 1H) | 461 | Meth 72 |
| 9[1,4] | Et | MeOCH2— | NH-CH2CH2-O-CH3 | 1.30(t, 3H), 2.88(q, 2H), 3.18(s, 3H), 3.33(t, 2H), 3.45(s, 3H), 4.77 (q, 2H), 4.85(s, 2H), 7.40(d, 1H), 7.55(t, 1H), 7.73(d, 2H), 7.90(d, 2H), 8.43(s, 1H), 8.67(d, 1H), 10.12(s, 1H) | 447 | Meth 72 |
| 10[1,2] | Me | MeOCH2— | NH-CH2-cyclopropyl | 0.07(m, 2H), 0.35(m, 2H), 0.80 (m, 1H), 2.63(t, 2H), 3.30(s, 3H), 4.02(s, 3H), 4.55(s, 2H), 7.25(d, 1H), 7.50(t, 1H), 7.70(m, 3H), 7.90(d, 2H), 8.48(d, 1H), 9.95(s, 1H) | 429 | Meth 70 |
| 11[1,4] | Me | MeOCH2— | NH-cyclobutyl | 1.52(m, 2H), 1.75(m, 2H), 1.91 (m, 2H), 3.31(s, 3H), 3.61(m, 1H), 4.03(s, 3H), 4.55(s, 2H), 7.28(d, 1H), 7.70(m, 4H), 7.90(d, 2H), 8.51(d, 1H), 9.98(s, 1H) | 429 | Meth 70 |

-continued

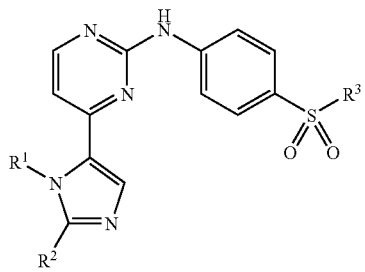

| Ex | R¹ | R² | R³ | NMR | M/z | SM |
|---|---|---|---|---|---|---|
| 12 | i-Pr | MeOCH₂— | NH~~~O~~~ | 1.06(t, 3H), 1.53(d, 6H), 2.84(m, 2H), 3.16(m, 4H), 3.48(s, 3H), 4.92(s, 2H), 5.55(m, 1H), 7.27(d, 1H), 7.53(m, 1H), 7.74(d, 2H), 7.89(d, 2H), 8.27(s, 1H), 8.71(d, 1H), 10.19(s, 1H) | 476 | Meth 69 |
| 13[1,6] | Me | i-Pr | NH~~~O~~~ | 1.05(t, 3H), 1.40(d, 6H), 2.88(br q, 2H), 3.33(m, 4H), 3.55(br s), 4.19(s, 3H), 7.41(d, 1H), 7.57(br t, 1H), 7.76(d, 2H), 7.94(d, 2H), 8.50(s, 1H), 8.70(d, 1H), 10.29(s, 1H) | 445 | Meth 71 |
| 14[1,7] | Me | i-Pr | NH~~~CF₃ | 1.41(d, 6H), 3.58(m, 1H), 3.68 (m, 2H), 4.20(s, 3H)(not integrated as covered by overlapping exchangeables), 7.42(d, 1H), 7.80 (d, 2H), 7.99(d, 2H), 8.48(t, 1H), 8.49(s, 1H), 8.70(d, 1H), 10.30(s, 1H), 15.00(v br s, 0.7H) | 455 | Meth 71 |
| 15[1,7] | Me | i-Pr | NH-t-Bu | 1.11(s, 9H), 1.41(d, 6H), 3.59(m, 1H), 4.18(s, 3H), 7.35(s, 1H), 7.41(d, 1H), 7.78(d, 2H), 7.91(d, 2H), 8.49(s, 1H), 8.70(d, 1H), 10.22(s, 1H) | 429 | Meth 71 |
| 16 | Me | Et | NH-t-Bu | 1.08(s, 9H), 1.32(t, 3H), 3.05(q, 2H), 4.08(s, 3H), 7.32(s, 1H), 7.36(d, 1H), 7.75(d, 2H), 7.89(d, 2H), 8.41(s, 1H), 8.68(d, 1H), 10.17(s, 1H) | 415 | 5 |
| 17 | Me | c-Pr | NH~~~O~~~ | 1.08(t, 3H), 1.27(m, 4H), 2.40(m, 1H), 2.89(m, 2H), 3.35(m, 4H), 4.21(s, 3H), 7.37(d, 1H), 7.50(m, 1H), 7.73(d, 2H), 7.93(d, 2H), 8.40(s, 1H), 8.65(d, 1H), 10.24(s, 1H) | 443 | Meth 79 |
| 18 | Me | c-Pr | NH~~~O~ | 1.26(m, 4H), 2.40(m, 1H), 2.87 (m, 2H), 3.18(s, 3H), 3.32(t, 2H), 4.21(s, 3H), 7.38(d, 1H), 7.53(m, 1H), 7.73(d, 2H), 7.93(d, 2H), 8.40(s, 1H), 8.65(d, 1H), 10.24(s, 1H) | 429 | Meth 79 |

-continued

| Ex | R¹ | R² | R³ | NMR | M/z | SM |
|----|----|----|----|----|-----|-----|
| 19 | Me | c-Pr | (tetrahydrofurfuryl-NHCH₂) | 1.26(m, 4H), 1.65(m, 4H), 2.40 (m, 1H), 2.78(m, 2H), 3.55(m, 1H), 3.70(m, 1H), 3.88(m, 1H), 4.21(s, 3H), 7.38(d, 1H), 7.53(m, 1H), 7.73(d, 2H), 7.93(d, 2H), 8.40(s, 1H), 8.67(d, 1H), 10.24(s, 1H) | 455 | Meth 79 |
| 20 | Me | c-Pr | cyclopropyl-NH | 0.30(m, 4H), 1.26(m, 4H), 1.65 (m, 4H), 2.13(m, 1H), 2.40(m, 1H), 4.21(s, 3H), 7.38(d, 1H), 7.73(m, 3H), 7.93(d, 2H), 8.40(s, 1H), 8.67(d, 1H), 10.22(s, 1H) | 411 | Meth 79 |
| 21 | n-Pr | c-Pr | NH-CH₂CH₂-O-Et | 0.70(t, 2H), 1.05(t, 3H), 1.29(m, 4H), 1.68(m, 2H), 2.50(m, 1H), 2.85(m, 2H), 3.33(m, 4H), 4.82(t, 2H), 7.38(d, 1H), 7.53(m, 1H), 7.73(d, 2H), 7.87(d, 2H), 8.40(s, 1H), 8.64(s, 1H), 10.17(s, 1H) | 471 | Meth 80 |
| 22 | n-Pr | c-Pr | NH-CH₂CH₂-OMe | 0.70(t, 2H), 1.32(m, 4H), 1.68(m, 2H), 2.50(m, 1H), 2.85(m, 2H), 3.17(s, 3H), 3.33(t, 2H), 4.82(t, 2H), 7.38(d, 1H), 7.53(m, 1H), 7.73(d, 2H), 7.87(d, 2H), 8.41(s, 1H), 8.64(s, 1H), 10.17(s, 1H) | 457 | Meth 80 |
| 23 | n-Pr | c-Pr | cyclopropyl-NH | 0.30(m, 4H), 0.70(t, 2H), 1.32(m, 4H), 1.68(m, 2H), 2.05(m, 1H), 2.50(m, 1H), 3.17(s, 3H), 4.83(t, 2H), 7.38(d, 1H), 7.74(m, 3H), 7.87(d, 2H), 8.41(s, 1H), 8.64(s, 1H), 10.17(s, 1H) | 439 | Meth 80 |

[1] Isolated as HCl salt
[2] Purified by flash silica chromatography DCM:MeOH(Polarity increasing from 100:0 to 97:3)
[3] Purified by Isolute amine column
[4] Purified by Isolute amine column followed by flash silica chromatography DCM:MeOH(Polarity increasing from 100:0 to 97:3)
[5] Example 29 of WO 02/20512
[6] Ethyldimethylamine used in place of diethylmethylamine. Work-up:- extracted with EtOAc, washed with dilute NaHCO₃, water and brine
[7] Ethyldimethylamine used in place of diethylmethylamine. Product purified by flash silica chromatography DCM:MeOH(96:4)

Example 24

4-(1-Methyl-2-isopropylimidazol-5-yl)-2-{4-[N-(cyclopropyl)sulphamoyl]anilino}pyrimidine Chlorosulphonic acid (150 μl, 2.16 mmol) was added dropwise to solution of 2-anilino-4-(1-methyl-2-isopropylimidazol-5-yl)pyrimidine (Method 71; 158 mg, 0.54 mmol) in thionyl chloride (3 ml) cooled at 0° C. and the mixture stirred at 0° C. for 10 minutes then heated at 90° C. for 90 minutes. The volatiles were removed by evaporation and the residue was dried under high vacuum (<2 mmHg) for 1 hour. The resulting solid was placed under nitrogen and a solution of cyclopropylamine (570 μl, 8.1 mmol) in MeOH (3 ml) added. The mixture was stirred for 30 minutes and the volatiles were evaporated in vacuo. Trituration with water results in a solid which was washed water (3×20 ml) collected by filtration and dried under vacuum at 60° C. to yield the title compound (205 mg, 92%) as a solid. NMR: 0.30 (m, 2H), 0.45 (m, 2H), 1.24 (d, 6H), 2.19 (m, 1H), 3.17 (m, 1H), 4.01 (s, 3H), 7.19 (d, 1H), 7.70 (d, 2H), 7.92 (d, 2H), 8.02 (m, 1H), 8.50 (d, 1H), 9.90 (brs, 1H); m/z 413.

Examples 25-71

The following compounds were prepared by the procedure of Example 24 using the appropriate starting materials.

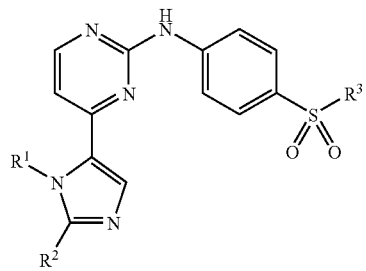

| Ex | R¹ | R² | R³ | NMR | M/z | SM |
|---|---|---|---|---|---|---|
| 25[1,2] | i-Pr | MeOCH₂— | NH–CH₂–cyclopropyl | 0.02(m, 2H), 0.38(m, 2H), 0.75(m, 1H), 1.52(d, 6H), 2.66(m, 2H), 3.43(s, 3H), 4.88(d, 2H), 5.52(m, 1H), 7.28(d, 1H), 7.53(m, 1H), 7.68(d, 2H), 7.83(d, 2H), 8.23(s, 1H), 8.68(d, 1H), 10.16(brs, 1H) | 457 | Meth 69 |
| 26[1,2] | i-Pr | MeOCH₂— | NH–cyclopropyl | 0.32(m, 2H), 0.53(m, 2H), 1.52(d, 6H), 2.07(m, 1H), 3.47(s, 3H), 4.92(d, 2H), 5.52(m, 1H), 7.28(d, 1H), 7.74(m, 3H), 7.83(d, 2H), 8.21(s, 1H), 8.68(d, 1H), 10.20(brs, 1H) | 443 | Meth 69 |
| 27[1,2] | i-Pr | MeOCH₂— | NH–CH₂CH₂–OMe | 1.52(d, 6H), 2.86(q, 2H), 3.16(s, 3H), 3.28(t, 2H), 3.43(s, 3H), 4.92(d, 2H), 5.52(m, 1H), 7.26(d, 1H), 7.56(m, 1H), 7.72(d, 2H), 7.88(d, 2H), 8.23(s, 1H), 8.70(d, 1H), 10.18(brs, 1H) | 461 | Meth 69 |
| 28[1,3] | Et | MeOCH₂— | NH–cyclopropyl | 0.38(m, 2H), 0.49(m, 2H), 1.32(t, 3H), 2.15(brs, 1H), 3.45(s, 3H), 4.80(q, 2H), 4.88(s, 2H), 7.45(d, 1H), 7.78(d, 3H), 7.95(d, 2H), 8.50(s, 1H), 8.70(d, 1H), 10.20(s, 1H) | 429 | Meth 72 |
| 29[1,4] | Et | MeOCH₂— | NH–C(CH₃)₃ | 1.10(s, 9H), 1.27(t, 3H), 3.43(s, 3H), 4.78(q, 2H), 4.86(s, 2H), 7.33(s, 1H), 7.40(d, 1H), 7.76(d, 2H), 7.86(d, 2H), 8.49(s, 1H), 8.69(d, 1H), 10.11(s, 1H) | 445 | Meth 72 |
| 30[1,3] | Et | Et | NH–cyclopropyl | 0.35(m, 2H), 0.48(m, 2H), 1.25(t, 3H), 1.39(t, 3H), 2.09(s, 1H), 3.08(q, 2H), 4.78(q, 2H), 7.40(d, 1H), 7.75(d, 3H), 7.92(d, 2H), 8.49(s, 1H), 8.67(d, 1H), 10.16(s, 1H) | 413 | Meth 73 |
| 31[1,3] | Et | Et | NH–CH₂CH=CH₂ | 1.25(t, 3H), 1.36(t, 3H), 3.08(q, 2H), 3.40(m, 2H), 4.76(q, 2H), 5.00(m, 1H), 5.12(m, 1H), 5.67(m, 1H), 7.40(d, 1H), 7.64(br t, 1H), 7.73(d, 2H), 7.88(d, 2H), 8.49(s, 1H), 8.65(d, 1H), 10.16(s, 1H) | 413 | Meth 73 |
| 32[1,4] | Me | MeOCH₂— | NH–cyclopropyl | 0.37(m, 2H), 0.48(m, 2H), 2.12(brs, 1H), 3.30(s, 3H), 4.03(s, 3H), 4.55(s, 2H), 7.29(d, 1H), 7.68(m, 4H), 7.95(d, 2H), 8.52(d, 1H), 10.00(s, 1H) | 415 | Meth 70 |

-continued

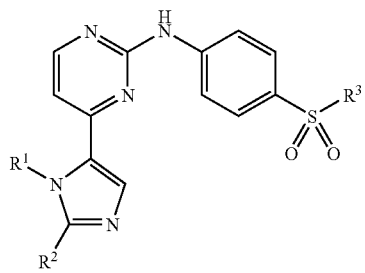

| Ex | R[1] | R[2] | R[3] | NMR | M/z | SM |
|---|---|---|---|---|---|---|
| 33[5] | Me | t-Bu—(CH$_2$)$_2$— | NH~~~O~ (methoxyethyl) | 0.98(s, 9H), 1.60(m, 2H), 2.78(m, 2H), 2.89(q, 2H), 3.18(s, 3H), 3.30(m, 2H), 3.99(s, 3H), 7.20(d, 1H), 7.44 (t, 1H), 7.63(s, 1H), 7.70(d, 2H), 7.93(d, 2H), 8.43(d, 1H), 9.90(s, 1H) | 473 | Meth 104 |
| 34[5] | Me | t-Bu—(CH$_2$)$_2$— | NH~~~O~ (ethoxyethyl) | 0.98(s, 9H), 1.04(t, 3H), 1.60 (m, 2H), 2.68(m, 2H), 2.87 (m, 2H), 3.30(m, 4H), 3.98(s, 3H), 7.20(d, 1H), 7.42(t, 1H), 7.64(s, 1H), 7.71(d, 2H), 7.92 (d, 2H), 8.43(d, 1H), 9.90(s, 1H) | 487 | Meth 104 |
| 35[2] | Me | n-Bu | NH~~~O~ (ethoxyethyl) | 0.90(3H, t), 1.04(3H, t), 1.38 (2H, m), 1.66(2H, m), 2.74 (2H, t), 2.88(2H, q), 3.32(4H, m), 3.98(3H, s), 7.18(1H, d), 7.42(1H, t), 7.71(2H, d), 7.92 (2H, d), 8.44(1H, d), 9.90 (1H, s) | 459 | Meth 89 |
| 36[2] | Me | n-Bu | NH~~~O~ (methoxyethyl) | 0.92(3H, t), 1.39(2H, m), 1.68(2H, m), 2.74(2H, t), 2.88(2H, q), 3.16(3H, s), 3.28 (2H, hidden), 3.96(3H, s), 7.19(1H, d), 7.46(1H, t), 7.64 (1H, s), 7.70(2H, d), 7.92(2H, d), 8.42(1H, d), 9.90(1H, s) | 445 | Meth 89 |
| 37 | i-Pr | i-Pr | NH~~~O~ (methoxyethyl) | 1.44(d, 6H), 1.58(d, 6H), 2.86 (m, 2H), 3.18(s, 3H), 3.27(t, 2H), 3.70(m, 1H), 5.60(m, 1H), 7.26(d, 1H), 7.57(brs, 1H), 7.73(d, 2H), 7.92(d, 2H), 8.28(s, 1H), 8.72(d, 1H), 10.21(brs, 1H) | 459 | Meth 76 |
| 38 | Me | Et | NH~~~O~ (ethoxyethyl) | 1.04(t, 3H), 1.36(t, 3H), 2.88 (m, 2H), 3.04(q, 2H), 3.34(m, 4H), 4.12(s, 3H), 7.38(d, 1H), 7.57(brs, 1H), 7.74(d, 2H), 7.92(d, 2H), 8.42(s, 1H), 8.68 (d, 1H), 10.23(brs, 1H) | 431 | 7 |
| 39 | i-Pr | i-Pr | NH~~~O~ (ethoxyethyl) | 1.03(t, 3H), 1.42(d, 6H), 1.57 (d, 6H), 2.84(m, 2H), 3.34(m, 4H), 3.69(m, 1H), 5.59(m, 1H), 7.25(d, 1H), 7.53(brs, 1H), 7.72(d, 2H), 7.89(d, 2H), 8.26(s, 1H), 8.72(d, 1H), 10.19(brs, 1H) | 473 | Meth 76 |
| 40 | Et | i-Pr | NH~~~O~ (methoxyethyl) | 1.33(t, 3H), 1.42(d, 6H), 3.09 (m, 3H), 3.25(s, 3H), 3.42(t, 2H), 4.63(q, 2H), 4.86(t, 1H), 7.04(d, 1H), 7.29(s, 1H), 7.59 (s, 1H), 7.75(d, 2H), 7.81(d, 2H), 8.38(s, 1H) | 446 | Meth 77 |

-continued

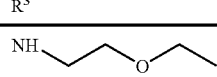

| Ex | R¹ | R² | R³ | NMR | M/z | SM |
|---|---|---|---|---|---|---|
| 41 | Et | i-Pr | 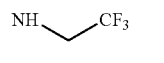 | 1.02(t, 3H), 1.13(t, 3H), 1.42 (d, 6H), 2.83(m, 2H), 3.33(m, 4H), 3.58(m, 1H), 4.81(q, 2H), 7.41(d, 1H), 7.59(brs, 1H), 7.72(d, 2H), 7.91(d, 2H), 8.58(s, 1H), 8.63(d, 1H) | 460 | Meth 77 |
| 42[6] | Et | MeOCH₂— | 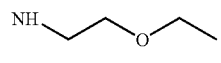 | 1.30(t, 3H), 3.41(s, 3H), 3.66 (quintet, 2H), 4.75(q, 2H), 4.83(s, 2H), 7.40(d, 1H), 7.77 (d, 2H), 7.90(d, 2H), 8.35(m, 2H), 8.66(d, 1H), 10.07(s, 1H) | 471 | Meth 72 |
| 43[6] | Me | MeOCH₂— | 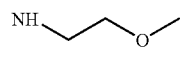 | 1.03(t, 3H), 2.90(m, 2H), 3.32(q, 4H), 3.45(s, 3H), 4.13 (s, 3H), 4.87(s, 2H), 7.41(d, 1H), 7.54(s, 1H), 7.75(d, 2H), 7.93(d, 2H), 8.46(s, 1H), 8.70 (d, 1H), 10.26(s, 1H) | 447 | Meth 70 |
| 44[6] | i-Pr | c-Pr | 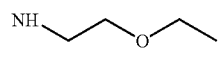 | 1.30(m, 2H), 1.41(m, 2H), 1.67(d, 6H), 2.58(m, 1H), 2.92(q, 2H), 3.20(s, 3H), 3.33 (t, 2H), 5.75(quintet, 1H), 7.31(d, 1H), 7.60(t, 1H), 7.79 (d, 2H), 7.91(d, 2H), 8.20(s, 1H), 8.73(d, 1H), 10.23(s, 1H) | 457 | Meth 81 |
| 45[6] | i-Pr | c-Pr | 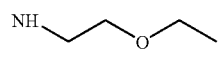 | 1.09(t, 3H), 1.35(m, 2H), 1.41(m, 2H), 1.67(d, 6H), 2.57(m, 1H), 2.91(q, 2H), 3.38(m, 4H), 5.71(quintet, 1H), 7.30(d, 1H), 7.58(t, 1H), 7.76(d, 2H), 7.90(d, 2H), 8.20 (s, 1H), 8.72(d, 1H), 10.21(s, 1H) | 471 | Meth 81 |
| 46[6] | Et | c-Pr | 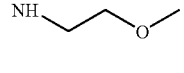 | 1.06(t, 3H), 1.30(m, 7H), 2.48(m, 1H), 2.89(q, 2H), 3.34(m, 4H), 4.88(q, 2H), 7.39(d, 1H), 7.53(t, 1H), 7.74 (d, 2H), 7.90(d, 2H), 8.40(s, 1H), 8.66(d, 1H), 10.12(s, 1H) | 457 | Meth 82 |
| 47[6] | Et | c-Pr | 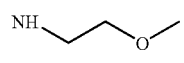 | 1.25(m, 4H), 1.35(t, 3H), 2.45(m, 1H), 2.89(q, 2H), 3.17(s, 3H), 3.30(t, 2H), 4.88 (q, 2H), 7.40(d, 1H), 7.55(t, 1H), 7.75(d, 2H), 7.90(d, 2H), 8.41(s, 1H), 8.67(d, 1H), 10.12(s, 1H) | 443 | Meth 82 |
| 48 | n-Pr | MeOCH₂— |  | (400 MHz) 0.71(t, 3H), 1.60 (sext, 2H), 2.89(q, 2H), 3.19 (s, 3H), 3.32(q, 2H), 3.43(s, 3H), 4.67(t, 2H), 4.83(s, 2H), 7.37(d, 1H), 7.53(t, 1H), 7.72 (d, 2H), 7.87(d, 2H), 8.35(s, 1H), 8.64(d, 1H), 10.10(s, 1H) | 461 | Meth 75 |

-continued

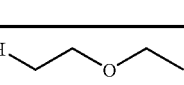

| Ex | R¹ | R² | R³ | NMR | M/z | SM |
|---|---|---|---|---|---|---|
| 49 | n-Pr | MeOCH₂— | NH~~~O~~ | (400 MHz) 0.69(t, 3H), 1.07(t, 3H), 1.61(sext, 2H), 2.89(q, 2H), 3.34(m, 4H), 3.42(s, 3H), 4.68(t, 2H), 4.81(s, 2H), 7.37(t, 1H), 7.52(t, 1H), 7.73 (d, 2H), 7.88(d, 2H), 8.36(s, 1H), 8.68(s, 1H), 10.13(s, 1H) | 475 | Meth 75 |
| 50[8] | Me | n-Pr | NH~~~O~ | 0.97(t, 3H), 1.70(m, 2H), 2.70(t, 2H), 2.89(q, 2H), 3.17 (s, 3H), 3.28(t, 2H), 3.95(s, 3H), 7.20(d, 1H), 7.44(t, 1H), 7.64(s, 1H), 7.70(d, 2H), 7.92 (d, 2H), 8.42(d, 1H), 9.89(s, 1H) | 431 | Meth 91 |
| 51[8] | Me | n-Pr | NH~~~O~~ | 0.98(t, 3H), 1.04(t, 3H), 1.70 (m, 2H), 2.70(t, 2H), 2.86(q, 2H), 3.31(m, 4H), 3.97(s, 3H), 7.19(d, 1H), 7.44(t, 1H), 7.64(s, 1H), 7.70(d, 2H), 7.92 (d, 1H), 8.42(d, 1H), 9.90(s, 1H) | 445 | Meth 91 |
| 52[9] | Me | MeO(CH₂)₂— | NH~~~O~ | 3.05(t, 2H), 3.15(q, 2H), 3.29 (s, 3H), 3.38(s, 3H), 3.44(t, 2H), 3.84(t, 2H), 4.0(s, 3H), 4.92(t, 1H), 7.02(d, 1H), 7.41 (br s, 1H), 7.59(s, 1H), 7.80 (m, 4H), 8.40(d, 1H) | 447 | Meth 92 |
| 53[9] | Me | MeO(CH₂)₂— | NH~~~O~~ | 1.15(t, 3H), 3.05(t, 2H), 3.14 (q, 2H), 3.38(s, 3H), 3.44(m, 4H), 3.84(t, 2H), 3.98(s, 3H), 5.01(t, 1H), 7.04(d, 1H), 7.50 (br s, 1H), 7.80(m, 4H), 8.40 (d, 1H) | 461 | Meth 92 |
| 54 | Et | n-Pr | NH~~~O~ | 0.98(t, 3H), 1.19(t, 3H), 1.75 (q, 2H), 2.69(t, 2H), 2.88(q, 2H), 3.30(t, 2H), 4.59(m, 2H), 7.22(d, 1H), 7.46(t, 1H), 7.74(m, 3H), 7.88(d, 2H), 8.42(d, 1H), 9.83(s, 1H) | 445 | Meth 93 |
| 55 | Et | n-Pr | NH~~~O~~ | 0.98(t, 3H), 1.06(t, 3H), 1.19 (t, 3H), 1.74(m, 2H), 2.70(t, 2H), 2.88(q, 2H), 3.36(m, 4H), 4.59(m, 2H), 7.22(d, 1H), 7.44(t, 1H), 7.70(m, 3H), 7.88(d, 2H), 8.42(d, 1H), 9.82(s, 1H) | 458 | Meth 93 |
| 56 | Et | n-Bu | NH~~~O~ | 0.97(t, 3H), 1.18(t, 3H), 1.40 (m, 2H), 1.70(m, 2H), 2.72(t, 2H), 2.88(q, 2H), 3.17(s, 3H), 3.27(t, 2H), 4.59(q, 2H), 7.21 (d, 1H), 7.44(t, 1H), 7.70(s, 1H), 7.72(d, 2H), 8.42(d, 1H), 9.81(s, 1H) | 458 | Meth 94 |

-continued

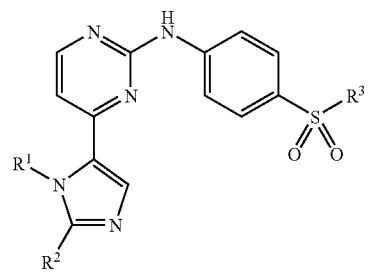

| Ex | R¹ | R² | R³ | NMR | M/z | SM |
|---|---|---|---|---|---|---|
| 57 | Et | n-Bu | NH~~~O~~~ | 0.92(t, 3H), 1.06(t, 3H), 1.18 (t, 3H), 1.38(m, 2H), 1.69(m, 2H), 2.74(t, 2H), 2.88(q, 2H), 3.37(m, 2H), 4.58(q, 2H), 7.20(d, 1H), 7.43(t, 1H), 7.68 (s, 1H), 7.70(d, 2H), 7.84(d, 2H), 8.42(d, 1H), 9.82(s, 1H) | 473 | Meth 94 |
| 58⁸ | i-Pr | n-Pr | NH~~~O~ | 1.0(t, 1H), 1.48(d, 6H), 1.79 (m, 2H), 2.78(t, 2H), 2.86(m, 2H), 3.30(t, 2H), 5.59(m, 1H), 7.15(d, 1H), 7.45(m, 2H), 7.78(d, 2H), 7.88(d, 2H), 8.44(d, 1H), 9.86(s, 1H) | 459 | Meth 95 |
| 59⁸ | i-Pr | n-Pr | NH~~~O~~~ | 1.0(m, 6H), 1.48(d, 6H), 1.78 (m, 2H), 2.77(t, 2H), 2.85(q, 2H), 3.32(m, 4H), 5.58(m, 1H), 7.16(d, 1H), 7.44(m, 2H), 7.69(d, 2H), 7.88(d, 2H), 8.45(d, 1H), 9.85(s, 1H) | 473 | Meth 95 |
| 60⁸ | i-Pr | Et | NH~~~O~ | 1.28(t, 3H), 2.48(d, 6H), 2.86 (m, 4H), 3.29(t, 2H), 5.59(m, 1H), 7.15(d, 1H), 7.44(m, 2H), 7.70(d, 2H), 7.86(d, 2H), 8.45(d, 1H), 9.84(s, 1H) | 445 | Meth 96 |
| 61⁸ | i-Pr | Et | NH~~~O~~~ | 1.04(t, 3H), 1.28(t, 3H), 1.46 (d, 6H), 2.82(m, 4H), 3.35(m, 4H), 5.59(m, 1H), 7.15(d, 1H), 7.24(m, 2H), 7.69(d, 2H), 7.86(d, 2H), 8.43(d, 1H), 9.85(s, 1H) | 459 | Meth 96 |
| 62 | i-Pr | EtOCH₂— | NH~~~O~ | 1.20(t, 3H), 1.52(d, 6H), 2.86 (m, 2H), 3.15(s, 3H), 3.29(t, 2H), 3.63(m, 2H), 4.92(s, 2H), 5.52(m, 1H), 7.27(d, 1H), 7.53(t, 1H), 7.71(d, 2H), 7.87(d, 2H), 8.22(s, 1H), 8.70 (d, 1H), 10.16(s, 1H) | 475 | Meth 78 |
| 63 | Me | i-PrCH₂— | NH~~~O~ | 0.96(d, 6H), 2.15–2.08(m, 1H), 2.61(d, 2H), 2.88(q, 2H), 3.18(s, 3H), 3.30–3.25 (m, 2H), 3.98(s, 3H), 7.20(d, 1H), 7.44(t, 1H), 7.64(s, 1H), 7.72(d, 2H), 7.92(d, 2H), 8.42 (d, 1H), 9.90(s, 1H) | 445 | Meth 109 |
| 64 | Me | i-PrCH₂— | NH~~~O~~~ | 0.95(d, 6H), 1.03(t, 3H), 2.15–2.07(m, 1H), 2.30(d, 2H), 2.88(q, 2H), 3.18(d, 2H), 3.38–3.30(m, 2H), 3.98 (s, 3H), 7.20(d, 1H), 7.43(t, 1H), 7.73–7.64(m, 3H), 7.90 (d, 2H), 8.42(d, 1H), 9.90(s, 1H) | 459 | Meth 109 |

-continued

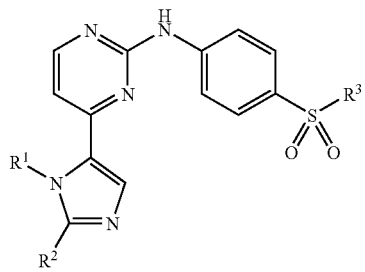

| Ex | R¹ | R² | R³ | NMR | M/z | SM |
|---|---|---|---|---|---|---|
| 65 | n-Pr | n-Pr | NH-CH₂CH₂-O-CH₃ | 0.62(t, 3H), 1.0(t, 3H), 1.51 (q, 2H), 1.75(q, 2H), 2.70(t, 2H), 2.89(q, 2H), 3.18(s, 3H), 3.30–3.25(m, 2H), 4.52(t, 2H), 7.20(d, 1H), 7.48(t, 1H), 7.74–7.65(m, 3H), 7.88(d, 2H), 8.42(d, 1H), 9.82(s, 1H) | 459 | Meth 99 |
| 66 | n-Pr | n-Pr | NH-CH₂CH₂-O-CH₂CH₃ | 0.68(t, 3H), 0.99(t, 3H), 1.04 (t, 3H), 1.50(q, 2H), 1.6(q, 2H), 2.70(t, 2H), 2.92–2.85 (m, 2H), 3.39–3.28(m, 2H), 4.51(t, 2H), 7.20(d, 2H), 7.43 (t, 1H), 7.68(s, 1H), 7.70(d, 2H), 7.88(d, 2H), 8.42(d, 1H), 9.82(s, 1H) | 473 | Meth 99 |
| 67 | n-Pr | t-Bu(CH₂)₂— | NH-CH₂CH₂-O-CH₃ | 0.70(t, 3H), 0.98(s, 9H), 1.46–1.64(m, 4H), 2.62–2.72(m, 2H), 2.87(q, 2H), 3.18(s, 3H), 3.27–3.30(m, 2H), 4.53(t, 2H), 7.20(d, 1H), 7.48(t, 1H), 7.63(s, 1H), 7.71(d, 2H), 7.87 (d, 2H), 8.42(s, 1H), 9.82(s, 1H) | 501 | Meth 115 |
| 68 | Et | n-Pr | NH-CH₂CH₂-OH | 0.96(t, 3H), 1.17(t, 3H), 1.73 (m, 2H), 2.69(t, 2H), 2.77(q, 2H), 3.35(q, 2H), 4.59(m, 3H), 7.21(d, 1H), 7.34(t, 1H), 7.69(m, 3H), 7.89(d, 2H), 8.41(d, 1H), 9.81(s, 1H) | 431 | Meth 93 |
| 69 | Et | n-Pr | NH₂ | 0.98(t, 3H), 1.25(t, 3H), 1.80 (m, 2H), 3.06(t, 2H), 4.78(q, 2H), 7.09(br s, 4H), 7.39(d, 1H), 7.75(d, 2H), 7.86(d, 2H), 8.51(s, 1H), 8.64(d, 1H), 10.14(s, 1H) | 387 | Meth 93 |
| 70¹⁰ | n-Pr | Me₂NCH₂— | NH-CH₂CH₂-O-CH₃ | 0.68(t, 3H), 1.54(q, 2H), 2.18 (s, 6H), 2.89(q, 2H), 3.17(s, 3H), 3.30(m, 2H), 3.53(s, 2H), 4.59(t, 2H), 7.22(d, 1H), 7.43(t, 1H), 7.66(s, 1H), 7.77 (d, 2H), 7.84(d, 2H), 8.44(d, 1H), 9.84(s, 1H) | 474 | Meth 119 |

-continued

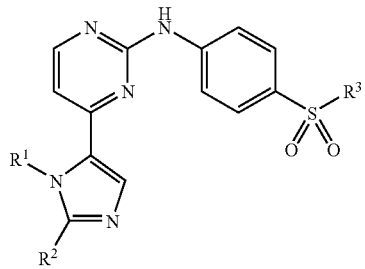

| Ex | R[1] | R[2] | R[3] | NMR | M/z | SM |
|---|---|---|---|---|---|---|
| 71[10] | n-Pr | EtNHCH$_2$— | NH~~~O/ (methoxyethyl) | 0.68(t, 3H), 1.05(t, 3H), 1.51 (m, 2H), 2.57(m, 2H), 2.88 (m, 2H), 3.18(s, 3H), 3.28(m, 2H), 3.80(s, 2H), 4.59(t, 2H), 7.20(d, 1H), 7.50(s, 1H), 7.68 (s, 1H) 7.70(d, 2H), 7.88(d, 2H), 8.43(d, 1H), 9.85(s, 1H) | 474 | Meth 120 |

[1]Isolated as HCl salt
[2]Purified by flash silica chromatography DCM:MeOH(Polarity increasing from 100:0 to 97:3)
[3]Purified by Isolute amine column
[4]Purified by Isolute amine column followed by flash silica chromatography DCM:MeOH(Polarity increasing from 100:0 to 97:3)
[5]Purified by flash silica chromatography DCM:MeOH(95:5)
[6]Purified by Isolute amine column followed by flash silica chromatography DCM:MeOH(Polarity increasing from 100:0 to 97:3) and isolated as the HCl salt
[7]Example 29 of WO 02/20512
[8]Purified by flash silica chromatography DCM:MeOH(98:2)
[9]Purified by flash silica chromatography DCM:MeOH(98.5:1.5)
[10]Purified by chromatography on silica gel eluting with DCM:MeOH(90:10)

Example 72

4-[1-(Methoxypropyl-2-yl)-2-(methoxymethyl)imidazol-5-yl]-2-{4-[N-(2-ethoxyethyl)sulphamoyl]anilino}pyrimidine To a stirred solution of 2-amino-4-(1-methoxyisopropyl-2-methoxymethylimidazol-5-yl)pyrimidine (Method 85; 163 mg, 0.6 mmol), N-(2-ethoxyethyl)-4-iodobenzenesulphonamide (Method 1; 400 mg, 1.2 mmol), tris(dibenzylideneacetone) dipalladium (0) (35 mg, 0.038 mmol) and 2,2'-bis (diphenylphosphino)-1,1'-binaphthyl (47 mg, 0.076 mmol) in dioxane (10 ml) was added sodium t-butoxide (258 mg, 2.69 mmol) and the mixture heated at 80° C. overnight. The reaction was cooled to room temperature and MeOH (5 ml) was added and the mixture poured onto an Isolute SCX-2 column, eluted first with MeOH (10×30 ml) and the product was then eluted with 5% methanolic ammonia (10×30 ml). The solvent was removed by evaporation and the residue purified by flash chromatography on silica gel eluting with DCM/MeOH (100:0 increasing in polarity to 97:3) to yield a foam which was dissolved in MeOH (2 ml) and treated with 1N HCl in ether (350 μl, 0.35 mmol) for 5 minutes. Solvent was evaporated in vacuo to yield a yellow foam which was triturated with ether to yield after filtration the title compound as a yellow solid (63 mg, 20%) NMR: 1.02 (t, 3H), 1.54 (d, 3H), 2.87 (m, 2H), 3.14 (s, 3H), 3.30 (m, 4H), 3.43 (s, 3H), 3.55 (m, 1H), 3.75 (m, 1H), 4.90 (s, 2H), 5.65 (m, 1H), 7.26 (d, 1H), 7.54 (m, 1H), 7.71 (d, 2H), 7.88 (d, 2H), 8.26 (s, 1H), 8.70 (d, 1H), 10.20 (brs, 1H); m/z 505.

Examples 73-74

The following compounds were prepared by the procedure of Example 72 using the appropriate starting materials.

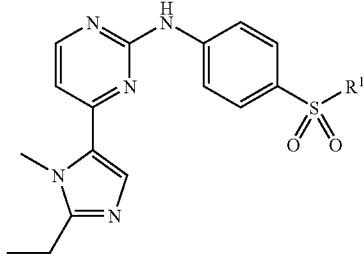

| Ex | R[1] | NMR | M/z | SM |
|---|---|---|---|---|
| 73 | NH~~~C(CF$_3$)F (structure with CF$_2$-CF$_3$) | 1.37(t, 3H), 3.06(q, 2H), 3.62(m, 2H), 4.12 (s, 3H), 7.39(d, 1H), 7.77(d, 1H), 7.94(d, 1H), 8.42(s, 1H), 8.44 (t, 1H), 8.65(d, 1H), 10.28(brs, 1H) | 441 | Meth 86 Meth 2 |
| 74 | NH~~~~O~ | 1.35(t, 3H), 1.58(m, 2H), 2.76(m, 2H), 3.04 (q, 2H), 3.17(s, 3H), 3.24(t, 2H), 4.10(s, 3H), 7.37(d, 1H), 7.39 (t, 1H), 7.71(d, 1H), 7.92(d, 1H), 8.39(s, 1H), 8.66(d, 1H), 10.21 (brs, 1H) | 431 | Meth 86 Meth 3 |

Example 75

2-{4-[N-(2-Methoxyethyl)sulphamoyl]anilino}-4-[1-methyl-2-(2-methyl-2-hydroxypropyl)imidazol-5-yl]pyrimidine The title compound was prepared by the procedure of Method 89 using Example 35 of WO 02/20512 and acetone as the starting materials. NMR: 1.20 (s, 6H), 2.88-2.83 (m, 4H), 3.18-3.15 (m, 5H), 4.0 (s, 3H), 4.78 (s, 1H), 7.20 (d, 1H), 7.44 (t, 1H), 7.70-7.67 (m, 3H), 7.90 (d, 2H), 8.46 (d, 1H), 9.90 (s, 1H); m/z 461.

Example 76

4-[2-(Prop-1-enyl)-1-(isopropyl)imidazol-5-yl]-2-{4-[N-(2-methoxyethyl)sulphamoyl]anilino}pyrimidine n-Butyl lithium (656 μl of a 1.6 N solution in hexane, 1.05 mmol), was added dropwise to a solution of ethyl triphenylphosphonium iodide (437 mg, 1.05 mmol), in anhydrous THF (15 ml), under nitrogen at 0° C. A solution of 4-(2-formyl-1-isopropylimidazol-5-yl)-2-{4-[N-(2-methoxyethyl)-N-(2-trimethylsilylethoxymethyl)sulphamoyl]anilino}pyrimidine (Method 105; 300 mg, 0.523 mmol), in THF (5 ml), was then slowly added. The mixture was allowed to warm to ambient temperature and stirred for 18 hours. The volatiles were removed by evaporation and the residue dissolved in EtOAc (40 ml), washed with water (2×15 ml), brine (15 ml), and dried. The solvent removed by evaporation to give a crude product (254 mg), as a yellow foam. The crude product was purified by chromatography on silica-gel eluting with 3% MeOH in DCM), the semi-pure product (70 mg), was dissolved in TFA/H$_2$O (1:1, 10 ml), and stirred for 1 hour. The TFA was removed by evaporation, the resulting aqueous solution neutralised with saturated NaHCO$_3$, and the product extracted with DCM (3×5 ml). The extracts were combined, dried and the solvent removed. The residue was purified by preparative reverse phase HPLC, eluting with acetonitrile/H$_2$O, 0.01% formic buffer. Pure fractions were neutralised with 2N aqueous sodium hydroxide solution. The resulting white precipitate, was collected by filtration and dried to give the title compound (1:2.5 mixture of E:Z isomers), as a white solid (5 mg, 2%). NMR: Z isomer 1.51 (d, 6H), 2.09 (d, 3H), 2.92 (t, 2H), 3.17 (s, 3H), 3.33 (t, 2H), 5.60 (m, 1H), 6.05 (m, 1H), 6.51 (m, 1H), 7.1 (br s, 1H), 7.16 (d, 1H), 7.57 (s, 1H), 7.71 (d, 2H), 7.88 (d, 2H), 8.48 (d, 1H), 9.47 (s, 1H); E isomer 1.51 (d, 6H), 1.94 (d, 3H), 2.92 (t, 2H), 3.17 (s, 3H), 3.33 (t, 2H), 5.60 (m, 1H), 6.60 (m, 1H), 6.67 (m, 1H), 7.1 (br s, 1H), 7.13 (d, 1H), 7.47 (s, 1H), 7.71 (d, 2H), 7.88 (d, 2H), 8.44 (d, 1H), 9.47 (s, 1H); m/z: 457.

Example 77

4-[2-(2-Methylprop-1-enyl)-1-ethylimidazol-5-yl]-2-{4-[N-(2-methoxyethyl)sulphamoyl]anilino}pyrimidine Aqueous TFA (90%) was added to a mixture of 4-[2-(2-methylprop-1-enyl)-1-ethylimidazol-5-yl]-2-{4-[N-(2-methoxyethyl)-N-t-butylsulphamoyl]anilino}pyrimidine (Method 111; 70 mg, 0.14 mmol), and anisole (90 μl, 0.83 mmol), and the mixture stirred at ambient temperature for 1 hour. The volatiles were evaporated and the residue dissolved in water. The solution was neutralised (NaHCO$_3$), and extracted with EtOAc. The extracts were dried, and the solvent evaporated to give the title compound (30 mg, 41%). NMR: 1.19 (t, 3H), 1.99 (s, 3H), 2.15 (s, 3H), 2.89 (q, 2H), 3.18 (s, 3H), 3.30-3.28 (m, 2H), 4.65 (q, 2H), 6.28 (s, 1H), 7.25 (d, 1H), 7.50 (t, 1H), 7.70 (d, 2H), 7.85 (s, 1H), 7.89 (d, 2H), 8.45 (d, 1H), 9.85 (s, 1H); m/z: 457.

Example 78

4-[2-(2-Methylprop-1-enyl)-1-methylimidazol-5-yl]-2-{4-[N-(2-methoxyethyl)sulphamoyl]anilino}pyrimidine 2-{4-[N-(2-Methoxyethyl)sulphamoyl]anilino}4-[t-methyl-2-(2-methyl-2-hydroxypropyl)imidazol-5-yl]pyrimidine (Example 75), was treated by the procedure described in Method 110 to give the title compound (30 mg, 14%). NMR: 1.99 (s, 3H), 2.15 (s, 3H), 2.87 (q, 2H), 3.18 (s, 3H), 3.23-3.30 (m, 2H), 4.0 (s, 3H), 6.26 (s, 1H), 7.22 (d, 1H), 7.43 (t, 1H), 7.70 (d, 2H), 7.79 (s, 1H), 7.92 (d, 2H), 8.44 (d, 1H), 9.90 (s, 1H); m/z: 443.

Example 79

4-[2-(But-3-en-1-yl)-1-propylimidazol-5-yl]-2-{4-[N-(2-methoxyethyl)sulphamoyl]anilino}pyrimidine A mixture of caesium fluoride (180 mg, 1.2 mmole), and 4-(2-(but-3-enyl)-1-propylimidazol-5-yl)-2-{4-[N-(2-methoxyethyl)-N-(2-trimethylsilylethoxymethyl)sulphamoyl]anilino}pyrimidine (Method 100; 100 mg, 0.17 mmol), in DMF (3 ml), was heated at 140° C. under nitrogen for 24 hours. The mixture was diluted with water and extracted with EtOAc. The extracts were washed with water and brine, dried, and the solvent evaporated. The residue was purified by chromatography on silica gel eluting with EtOAc to give the title compound. (8 mg, 10%). NMR: 0.7 (t, 3H), 1.52 (q, 2H), 2.80 (t, 2H), 2.85-2.89 (m, 2H), 3.19 (s, 3H), 3.18-3.22 (m, 2H), 3.30 (t, 2H), 4.52 (t, 2H), 4.98 (d, 1H), 5.10 (dd, 1H), 5.95-5.89 (m, 1H), 7.20 (d, 1H), 7.44 (t, 1H), 7.70 (s, 3H), 7.74 (d, 2H), 7.89 (d, 2H), 8.45 (d, 1H), 9.80 (s, 1H); m/z: 471.

Example 80

4-[2-(Methylthiomethyl)-1-(propyl)imidazol-5-yl]-2-{4-[N-(2-ethoxyethyl)sulphamoyl]anilino}pyrimidine Sodium thiomethoxide (21 mg, 0.3 mmol) was added to a stirred solution of 4-[2-(chloromethyl)-1-(propyl)imidazol-5-yl]-2-{4-[N-(2-methoxyethyl)sulphamoyl]anilino}pyrimidine (Method 116; 52 mg, 0.1 mmol) in MeOH (5 ml) and the solution was stirred at ambient temperature for 3 hour. The solvent was removed evaporation and the residue was partitioned between water and EtOAc. The organic phase was washed with saturated aqueous sodium hydrogen carbonate solution and brine, dried (Na$_2$SO$_4$) and the volatiles removed by evaporation. The residue was triturated with ether and collected by filtration. This solid was suspended in MeOH (2 ml) and 1.0M ethereal hydrogen chloride was added to give a clear solution. The volatiles were removed by evaporation and the residue triturated with ether giving the title compound (42 mg, 80%) as the hydrochloride salt. NMR: 0.72 (t, 3H), 1.06 (t, 3H), 1.63 (m, 2H), 2.18 (s, 3H), 2.88 (q, 2H), 3.35 (m, 4H), 4.42 (s, 2H), 4.72 (m, 2H), 7.37 (d, 1H), 7.54 (t, 1H), 7.75 (d, 2H), 7.89 (d, 2H), 8.39 (s, 1H), 8.68 (d, 1H), 10.14 (s, 1H); m/z 491.

Examples 81-82

The following compounds were prepared by the procedure of Example 80 using 4-[2-(chloromethyl)-1-(propyl)imidazol-5-yl]-2-{4-[N-(2-ethoxyethyl)sulphamoyl]anilino}pyrimidine (Method 116) and the appropriate reagent but without conversion of the free base product to hydrochloride salt.

| Ex | Compound | NMR | M/z [MH]+ |
|---|---|---|---|
| 81 | 4-[2-(Isopropylthiomethyl)-1-(propyl)imidazol-5-yl]-2-{4-[N-(2-ethoxyethyl)sulphamoyl]anilino}pyrimidine | 0.67(t, 3H), 1.03(t, 3H), 1.20(d, 6H), 1.55(m, 2H), 2.85(m, 2H), 2.93(m, 1H), 3.33(m, 4H), 3.94(s, 2H), 4.55(t, 2H), 7.21(d, 1H), 7.45(t, 1H), 7.68(s, 1H), 7.72(d, 2H), 7.84(d, 2H), 8.45(d, 1H), 9.85(s, 1H) | 519 |
| 82 | 4-[2-(Ethylthiomethyl)-1-(propyl)imidazol-5-yl]-2-{4-[N-(2-ethoxyethyl)sulphamoyl]anilino}pyrimidine | 0.68(t, 3H), 1.04(t, 3H), 1.17(t, 3H), 1.55(m, 2H), 2.53(m, 2H), 2.86(q, 2H), 3.33(m, 4H), 3.90(s, 2H), 4.55(t, 2H), 7.21(d, 1H), 7.45(t, 1H), 7.68(s, 1H), 7.72(d, 2H), 7.84(d, 2H), 8.45(d, 1H), 9.85(s, 1H) | 505 |

Example 83

4-[2-(Ethylsulphinylmethyl)-1-(propyl)imidazol-5-yl]-2-{4-[N-(2-ethoxyethyl)sulphamoyl]anilino}pyrimidine A solution of sodium periodate (43 mg, 0.2 mmol) in water (0.5 ml) was added to a stirred solution of 4-[2-(ethylthiomethyl)-1-(propyl)imidazol-5-yl]-2-{4-[N-(2-ethoxyethyl)sulphamoyl]anilino}pyrimidine (Example 82; 70 mg, 0.14 mmol) in MeOH (2 ml) and the solution was stirred for 18 hours. The MeOH was removed by evaporation and the aqueous residue was extracted with EtOAc. The extracts were combined, washed with brine, dried and the volatiles removed by evaporation. The residue was purified by chromatography on silica gel eluting with DCM/MeOH (95:5 increasing in polarity to 90:10) and the purified product triturated with ether to give the title compound (37 mg, 51%). NMR: 0.68 (t, 3H), 1.05 (t, 3H), 1.22 (t, 3H), 1.52 (m, 2H), 2.85 (m, 4H), 3.33 (m, 4H), 4.31 (d of d, 2H), 4.63 (m, 2H), 7.23 (d, 1H), 7.46 (t, 1H), 7.70 (d, 2H), 7.78 (s, 1H), 7.86 (d, 2H), 8.48 (d, 1H), 9.90 (s, 1H); m/z 521.

Example 84

4-[2-(Ethylsulphonylmethyl)-1-(propyl)imidazol-5-yl]-2-{4-[N-(2-ethoxyethyl)sulphamoyl]anilino}pyrimidine Oxone (123 mg, 0.2 mmol) was added to a stirred solution of 4-[2-(ethylthiomethyl)-1-(propyl)imidazol-5-yl]-2-{4-[N-(2-ethoxyethyl)sulphamoyl]anilino}pyrimidine (Example 82; 70 mg, 0.14 mmol) in MeOH/acetone/water (15:5:3) (2 ml) at 0-4° C. The solution was allowed to warm to ambient temperature and stirred for 2 hr. The reaction mixture was diluted with water and extracted with EtOAc. The extracts were combined, washed with brine, dried ($Na_2SO_4$) and the volatiles removed by evaporation. The residue was purified by chromatography on silica gel eluting with DCM/MeOH (95:5) and the purified product triturated with ether to give the title compound (44 mg, 59%). NMR: 0.65 (t, 3H), 1.03 (t, 3H), 1.27 (t, 3H), 1.52 (m, 2H), 2.85 (q, 2H), 3.30 (m, 6H), 4.64 (t, 2H), 4 81 (s, 2H), 7.25 (d, 1H), 7.46 (t, 1H), 7.70 (d, 2H), 7.79 (s, 1H), 7.97 (d, 2H), 8.50 (d, 1H), 9.91 (s, 1H); m/z 537.

Example 85

4-[2-(Isopropoxymethyl)-1-(propyl)imidazol-5-yl]-2-{4-[N-(2-ethoxyethyl)sulphamoyl]anilino}pyrimidine Sodium isopropoxide (87 mg, 1.05 mmol) was added to a stirred suspension of 4-[2-(chloromethyl)-1-(propyl)imidazol-5-yl]-2-{4-[N-(2-ethoxyethyl)sulphamoyl]anilino}pyrimidine (Method 116; 100 mg, 0.21 mmol) in isopropanol (20 ml). The reaction was stirred for 48 hours at ambient temperature, and was then poured into water (80 ml) and extracted with EtOAc (3×30 ml). The extracts were combined washed with brine (2×40 ml), dried and the volatiles removed by evaporation. The residue was purified by reverse phase HLPC (C18 column) eluting with aqueous ammonia/water/acetonitrile (5:90:5 decreasing in polarity to (5:0:95) to give the title compound (18 mg, 17%) as a brown gum. M/z 503.

Example 86

4-[2-(Phenethyl)-1-(methyl)imidazol-5-yl]-2-{4-[N-(2-methoxyethyl)sulphamoyl]anilino}pyrimidine 4-{2-[2-(4-Chlorophenyl)ethyl]-1-(methyl)imidazol-5-yl}-2-{4-[N-(2-methoxyethyl)sulphamoyl]anilino}pyrimidine (Method 117; 115 mg, 0.219 mmol) and triethylamine (34 µl, 0.241 mmol) was dissolved in ethanol (20 ml) and EtOAc (10 ml) and 30% palladium on charcoal catalyst (30 mg) added. The mixture was stirred for 3 days under an atmosphere of hydrogen. The catalyst was removed by filtration and filtrate evaporated. The residue was dissolved in DCM (20 ml), washed with water (2×5 ml), dried and the solvent removed by evaporation to give the title compound (67 mg, 63%) as a white solid. NMR: 2.88 (q, 2H) 3.05 (s, 4H) 3.16 (s, 3H) 3.28 (t, 3H) 3.90 (s, 3H) 7.21 (d, 1H) 7.28 (m, 5H) 7.69 (s, 1H) 7.70 (d, 2H) 8.44 (d, 1H) 9.94 (s, 1H); m/z 493.

Preparation of Starting Materials

The starting materials for the examples above are either commercially available or are readily prepared by standard methods from known materials. For example, the following reactions are an illustration, but not a limitation, of some of the starting materials used in the above reactions.

Method 1

N-(2-Ethoxyethyl)-4-iodobenzenesulphonamide

2-Ethoxyethylamine (2.14 g, 24 mmol) and diisopropylethylamine (4.2 ml, 24 mmol) were dissolved in DCM (50 ml) and cooled to 0° C. To this was added pipsyl chloride (6.05 g, 20 mmol) in portions and the reaction stirred for 18 hours. Volatiles were evaporated in vacuo. The residue was dissolved in EtOAc (50 ml), extracted 1N citric acid (2×50 ml), brine (50 ml), dried and evaporated in vacuo to yield an oil which solidified on standing to give the title compound as a pale yellow solid (6.97 g, 98%). NMR: 1.01 (t, 3H), 2.89 (q, 2H), 3.30 (m, 4H), 7.53 (d, 2H), 7.75 (t, 1H), 7.97 (d, 2H); m/z 354 (M–H)⁻.

Methods 2-5

The following compounds were prepared by the procedure of Method 1 using the appropriate starting materials.

| Meth | Compound | NMR | M/z |
|---|---|---|---|
| 2 | N-(2,2,2-trifluoroethyl)-4-iodosulphonamide | 3.69(q, 2H), 7.58(d, 2H), 7.93(d, 2H), 8.65(brs, 1H) | 364(M–H)⁻ |
| 3 | N-(3-Methoxypropyl)-4-iodobenzenesulphonamide | 1.68(m, 2H), 3.02(q, 2H), 3.21(s, 3H), 3.38(t, 2H), 5.10(s, 1H), 7.51(d, 2H), 7.80(d, 2H) | 356 |
| 4 | N-(2-Methoxyethyl)-4-iodobenzenesulphonamide | 3.14(q, 2H), 3.25(s, 3H), 3.40(q, 2H), 4.97(s, 1H), 7.58(d, 2H), 7.90(d, 2H) | 342 |
| 5 | N-t-Butyl-4-iodobenzenesulphonamide | 1.08(s, 9H), 7.56(m, 3H), 7.94(d, 2H) | 338[MH]⁻ |

Methods 6-7

The following compounds were synthesised by the procedure as described in JOC 1987, 2714-2716.

| Meth | Compound |
|---|---|
| 6 | 5-Methyl-4-(methylamino)isoxazole hydrochloride |
| 7 | 5-Acetyl-1-methyl-2-(methoxymethyl)imidazole |

Methods 8-49

The following compounds were prepared using procedures analogous to those described in JOC 1987, 2714-2726.

| Meth | Compound | NMR | M/z | SM |
|---|---|---|---|---|
| 8 | 5-Methyl-4-(N-methyl-N-propionylamino)isoxazole | 1.09(t, 3H), 2.08(q, 2H), 2.38(s, 3H), 3.16(s, 3H), 8.16(s, 1H) | 169 | Meth 6 |
| 9 | 1-Methyl-2-ethyl-5-acetylimidazole | 1.36(t, 3H), 2.41(s, 3H), 2.72(q, 2H), 3.82(s, 3H), 7.72(s, 1H) | 153 | Meth 8 |
| 10 | 4-(Isopropylamino)-5-methylisoxazole | (CDCl₃) 1.12(d, 6H), 2.30(s, 3H), 3.21(1H, sept), 8.01(s, 1H) | 141 | 4-Amino-5-methylisoxazole hydrochloride |

-continued

| Meth | Compound | NMR | M/z | SM |
|---|---|---|---|---|
| 11 | 5-Methyl-4-(N-isopropyl-N-methoxyacetamido)isoxazole | 0.95(d, 6H), 2.35(s, 3H), 3.20(s, 3H), 3.60(s, 2H), 4.70(m, 1H), 8.60(s, 1H) | 213 | Meth 10 |
| 12 | 1-isopropyl-2-methoxymethyl-5-acetylimidazole | 1.43(d, 6H), 2.40(s, 3H), 3.24(s, 3H), 4.50(s, 2H), 4.90(m, 1H), 7.92(s, 1H) | 197 | Meth 11 |
| 13 | 5-Methyl-4-(N-methyl-N-isobutyrylamino)isoxazole | 1.03(d, 6H), 2.36(s, 3H), 2.48(m, 1H), 3.16(s, 3H), 8.20(s, 1H) | 183 | Meth 6 |
| 14 | 1-Methyl-2-isopropyl-5-acetylimidazole | 1.36(d, 6H), 2.42(s, 3H), 3.10(m, 1H), 3.84(s, 3H), 7.75(s, 1H) | 167 | Meth 13 |
| 15 | 5-Methyl-4-(N-acetamido)isoxazole | 2.00(s, 3H), 2.34(s, 3H), 8.64(s, 1H), 9.60(brs, 1H) | 141 | 4-Amino-5-methylisoxazole hydrochloride |
| 16 | 5-Methyl-4-(ethylamino)isoxazole hydrochloride | 1.21(t, 3H), 2.58(s, 3H), 3.22(q, 2H), 8.76(s, 1H) | 127 | Meth 15 |
| 17 | 5-Methyl-4-(N-ethyl-N-methoxyacetamido)isoxazole | (CDCl$_3$) 1.12(t, 3H), 2.39(s, 3H), 3.36(s, 3H), 3.64(q, 2H), 3.75(s, 2H), 8.16(s, 1H) | 199 | Meth 16 |
| 18 | 5-Acetyl-1-ethyl-2-methoxymethyl imidazole | (CDCl$_3$) 1.37(t, 3H), 2.48(s, 3H), 3.38(s, 3H), 4.39(q, 2H), 4.56(s, 2H), 7.74(s, 1H) | 183 | Meth 17 |
| 19 | 5-Methyl-4-(N-ethyl-N-propylamido)isoxazole | (CDCl$_3$) 1.11(q, 6H), 2.05(q, 2H), 2.39(s, 3H), 3.65(q, 2H) 8.16(s, 1H) | 183 | 5-Methyl-4-(ethylamino)isoxazole hydrochloride |
| 20 | 5-Acetyl-1,2-diethylimidazole | (CDCl$_3$) 1.35(m, 6H), 2.45(s, 3H), 2.73(q, 2H), 4.30(q, 2H), 7.73(s, 1H) | 167 | Meth 19 |
| 21 | 5-Methyl-4-(methoxyisopropyl amino)isoxazole hydrochloride | 1.01(d, 3H), 2.06(s, 3H), 3.05(m, 2H), 3.19(m, 6H), 2.92(m, 1H), 8.26(s, 1H) | 171 | 4-Amino-5-methylisoxazole hydrochloride |
| 22 | 5-Methyl-4-(N-methoxyisopropyl-N-methoxyacetamido)isoxazole | 0.90(d, 3H), 2.35(s, 3H), 3.20(m, 8H), 3.60(s, 2H), 4.80(m, 1H), 8.40(m, 1H) | 243 | Meth 21 |
| 23 | 5-Acetyl-1-methoxyisopropyl-2-methoxymethyl imidazole | 1.38(d, 3H), 2.40(s, 3H), 3.16(s, 3H), 3.24(s, 3H), 3.58(m, 1H), 3.78(m, 1H), 4.50(q, 2H), 4.96(m, 1H), 7.97(s, 1H) | 227 | Meth 22 |
| 24 | 5-Methyl-4-(N-propyl-N-methoxyacetamido)isoxazole | 0.81(t, 3H), 1.37(sext, 2H), 2.34(s, 3H), 3.18(s, 3H), 3.42(t, 2H), 3.71(s, 2H), 8.65(s, 1H) | 213 | Meth 45 |
| 25 | 1-Propyl-2-methoxymethyl-5-acetylimidazole | 0.83(t, 3H), 1.62(sext, 2H), 2.40(s, 3H), 3.25(s, 3H), 4.18(t, 2H), 4.50(s, 2H), 7.90(s, 1H) | 197 | Meth 24 |
| 26 | 5-Methyl-4-(N-isopropyl-N-2-methylpropylamido)isoxazole | 1.02(br m, 12H), 2.32(m, 1H), 2.37(s, 3H), 4.98(m, 1H), 8.14(s, 1H) | 211 | Meth 10 |
| 27 | 1-Isopropyl-2-isopropyl-5-acetylimidazole | 1.38(d, 6H), 1.55(d, 6H), 2.43(s, 3H), 3.17(m, 1H), 5.18(m, 1H), 7.78(s, 1H) | 195 | Meth 26 |
| 28 | 5-Methyl-4-[N-ethyl-N-(2-methylpropyl-amido)]isoxazole | 1.04(d, 6H), 1.08(t, 3H), 2.38(s, 3H), 2.41(m, 1H), 3.60(q, 2H), 8.15(s, 1H) | 197 | Meth 16 |
| 29 | 1-Ethyl-2-isopropyl-5-acetylimidazole | 1.32(t, 3H), 1.34(d, 6H), 2.42(s, 3H), 3.01(m, 1H), 4.36(q, 2H), 7.77(s, 1H) | 182 | Meth 28 |

| Meth | Compound | NMR | M/z | SM |
|---|---|---|---|---|
| 30 | 5-Methyl-4-(N-isopropyl-N-ethoxyacetamido)isoxazole | 1.0(m, 9H), 2.34(s, 3H), 3.34(m, 2H), 3.61(s, 2H), 4.73(m, 1H), 8.58(s, 1H) | | Meth 10 |
| 31 | 1-Isopropyl-2-ethoxymethyl-5-acetylimidazole | 1.10(t, 3H), 1.43(d, 6H), 2.43(s, 3H), 3.44(m, 2H), 4.57(s, 2H), 4.96(m, 1H), 7.91(s, 1H) | | Meth 30 |
| 32 | 5-Methyl-4-(N-methyl-N-cyclopropylamido)isoxazole | 0.76(m, 4H), 1.42(m, 1H), 2.36(s, 3H), 3.07(s, 3H), 8.78(s, 1H) | 181 | 5-Methyl-4-(methylamino)isoxazole hydrochloride |
| 33 | 1-Methyl-2-cyclopropyl-5-acetylimidazole | 0.60(m, 4H), 1.72(m, 1H), 2.00(s, 3H), 3.55(s, 3H), 7.41(s, 1H) | 165 | Meth 32 |
| 34 | 5-Methyl-4-(N-propyl-N-cyclopropylamido)isoxazole | 0.80(m, 7H), 1.35(m, 3H), 2.32(s, 3H), 3.45(t, 2H), 8.76(s, 1H) | 209 | Meth 45 |
| 35 | 1-Propyl-2-cyclopropyl-5-acetylimidazole | 0.80(m, 7H), 1.65(m, 2H), 2.05(m, 1H), 2.38(s, 3H), 4.35(t, 2H), 7.80(s, 1H) | 193 | Meth 34 |
| 36 | 5-Methyl-4-(N-isopropyl-N-cyclopropylamido)isoxazole | 0.61(br s, 2H), 0.76(br s, 2H), 0.97(br s, 6H), 1.24(m, 1H), 2.36(s, 3H), 4.76(m, 1H), 8.66(s, 1H) | 209 | Meth 10 |
| 37 | 1-Isopropyl-2-cyclopropyl-5-acetylimidazole | 0.96(m, 4H), 1.49(d, 6H), 2.11(m, 1H), 2.37(s, 3H), 5.40(m, 1H), 7.77(s, 1H) | 193 | Meth 36 |
| 38 | 5-Methyl-4-(N-ethyl-N-cyclopropylamido)isoxazole | 0.70(m, 4H), 1.00(t, 3H), 1.36(m, 1H), 2.38(s, 3H), 3.54(q, 2H), 8.74(s, 1H) | 195 | Meth 16 |
| 39 | 1-Ethyl-2-cyclopropyl-5-acetylimidazole | 0.86(m, 2H), 0.97(m, 2H), 1.23(t, 3H), 2.04(m, 1H), 2.36(s, 3H), 4.39(q, 2H), 7.78(s, 1H) | 179 | Meth 38 |
| 40 | 5-Methyl-4-(N-propyl-N-acetamido)isoxazole | 0.81(t, 3H), 1.37(m, 2H), 1.75(s, 3H), 2.34(s, 3H), 3.42(t, 2H), 8.67(s, 1H) | 183 | Meth 45 |
| 41 | 1-Propyl-2-methyl-5-acetylimidazole | 0.83(t, 3H), 1.60(m, 2H), 2.37(m, 6H), 4.17(t, 2H), 7.83(s, 1H) | 167 | Meth 40 |
| 42 | 5-Methyl-4-(N-isopropylformido)isoxazole | Used crude | | Meth 10 |
| 43 | 5-Acetyl-1-isopropylimidazole | 1.38(d, 6H), 2.48(s, 3H), 5.13(q, 2H), 7.86(s, 1H), 8.10(s, 1H) | 153 | Meth 42 |
| 44 | 5-Methyl-4-(N-propylamido)isoxazole | 1.05(t, 3H), 2.28(q, 2H), 2.35(s, 3H), 8.65(s, 1H), 9.50(s, 1H) | 153[MH]− | 4-amino-5-methylisoxazole hydrochloride |
| 45 | 5-Methyl-4-(propylamino)isoxazole | 0.90(t, 3H), 1.62(m, 2H), 2.53(s, 3H), 3.10(t, 2H), 8.68(s, 1H) | 141 | Meth 44 |
| 46 | 5-Methyl-4-(N-propionylamido)isoxazole | 1.05(t, 3H), 2.28(q, 2H), 2.35(s, 3H), 8.65(s, 1H), 9.50(s, 1H) | 153[MH]− | 4-amino-5-methylisoxazole hydrochloride |
| 47 | 5-Methyl-4-(propylamino)isoxazole | 0.90(t, 3H), 1.62(m, 2H), 2.53(s, 3H), 3.10(t, 2H), 8.68(s, 1H) | 141 | Meth 46 |
| 48 | 5-Methyl-4-(N-propylformido)isoxazole | 0.82(m, 3H), 1.42(m, 2H), 2.28 & 2.38(s, 3H), 3.50(m, 2H), 8.08 & 8.23(2s, 1H), 8.62 & 8.72(s, 1H) | 167[MH]− | Meth 47 |
| 49 | 5-Acetyl-1-propylimidazole | 0.76(t, 3H), 1.63(m, 2H), 2.40(s, 3H), 4.28(t, 2H), 7.90(s, 1H), 7.95(s, 1H) | 153 | Meth 48 |

Method 50

5-(3-Dimethylaminoprop-2-en-1-oyl)-1-isopropyl-2-methoxymethylimidazole

1-Isopropyl-2-methoxymethyl-5-acetylimidazole (Method 12; 3.34 g, 17 mmol) was dissolved in a mixture of DMF (34 ml) and DMF.DEA (11.5 ml, 68 mmol) and the mixture heated under reflux, under an atmosphere of nitrogen, for 18 hours. The volatiles were removed by evaporation. A solid was precipitated with ether, collected by filtration and air dried to yield the title compound as a brown solid (2.25 g, 53%); NMR 1.43 (d, 6H), 2.95 (m, 6H), 3.20 (s, 3H), 4.46 (s, 2H), 5.00 (m, 1H), 5.56 (d, 1H), 7.55 (m, 2H); m/z 252.

Methods 51-68

The following compounds were prepared by the procedure of Method 50.

| Meth | Compound | NMR | M/z | SM |
|---|---|---|---|---|
| 51[1] | 5-(3-Dimethylaminoprop-2-en-1-oyl)-1-methyl-2-methoxymethylimidazole | 2.87(s, 3H), 3.05(s, 3H), 3.20(s, 3H), 3.83(s, 3H), 4.45(s, 2H), 5.58(d, 1H), 7.55(d, 1H), 7.59(s, 1H) | 224 | Meth 7 |
| 52[2] | 5-(3-Dimethylaminoprop-2-en-1-oyl)-1-methyl-2-ethylimidazole | 1.20(t, 3H), 2.62(q, 2H), 2.95(s, 6H), 3.78(s, 3H), 5.56(d, 1H), 7.51(m, 2H) | 208 | Meth 9 |
| 53[1] | 5-(3-Dimethylaminoprop-2-en-1-oyl)-1-methyl-2-isopropylimidazole | 1.20(d, 6H), 3.05(m, 1H), 3.80(s, 3H), 5.53(d, 1H), 7.50(m, 2H) | 222 | Meth 14 |
| 54 | 5-(3-Dimethylaminoprop-2-en-1-oyl)-1-ethyl-2-methoxymethylimidazole | 1.23(t, 3H), 2.96(m, 6H), 3.25(s, 3H), 4.36(q, 2H), 4.47(s, 2H), 5.60(d, 1H), 7.56(d, 1H), 7.63(s, 1H) | 222 | Meth 18 |
| 55 | 5-(3-Dimethylaminoprop-2-en-1-oyl)-1,2-diethylimidazole | 1.20(m, 6H), 2.65(q, 2H), 2.96(brs, 6H), 4.31(q, 2H), 5.57(d, 1H), 7.51(d, 1H), 7.57(s, 1H) | 238 | Meth 20 |
| 56 | 5-(3-Dimethylaminoprop-2-en-1-oyl)-1-methoxyisopropyl-2-methoxymethylimidazole | 1.40(d, 3H), 2.95(m, 6H), 3.16(s, 3H), 3.24(s, 3H), 3.63(m, 1H), 3.89(m, 1H), 4.47(q, 2H), 5.00(m, 1H), 5.58(d, 1H), 7.75(m, 2H) | 282 | Meth 23 |
| 57 | 5-(3-Dimethylaminoprop-2-en-1-oyl)-1,2-dimethylimidazole | 2.26(s, 3H), 2.95(brs, 6H), 3.8(s, 3H), 5.56(d, 1H), 7.52(m, 2H) | 194 | [3] |
| 58 | 5-(3-Dimethylaminoprop-2-en-1-oyl)-1-propyl-2-methoxymethylimidazole | 0.82(t, 3H), 1.62(sext, 2H), 2.7-3.3(br m, 6H), 3.24(s, 3H), 4.25(t, 2H), 4.45(s, 2H), 5.60(d, 1H), 7.56(d, 1H), 7.60(s, 1H) | 252 | Meth 25 |
| 59 | 5-(3-Dimethylaminoprop-2-en-1-oyl)-1-isopropyl-2-isopropylimidazole | 1.37(d, 6H), 1.58(d, 6H), 2.94(s, 6H), 3.16(m, 1H), 5.23(m, 1H), 5.53(d, 1H), 7.50(s, 1H), 7.62(d, 1H) | 250 | Meth 27 |
| 60 | 5-(3-Dimethylaminoprop-2-en-1-oyl)-1-ethyl-2-isopropylimidazole | 1.19(t, 3H), 1.21(d, 6H), 2.48(s, 6H), 3.03(m, 1H), 4.33(q, 2H), 5.57(d, 1H), 7.55(d, 1H), 7.57(s, 1H) | 237 | Meth 29 |
| 61 | 5-(3-Dimethylaminoprop-2-en-1-oyl)-1-isopropyl-2-ethoxymethylimidazole | 1.10(t, 3H), 1.28(d, 6H), 2.99(m, 6H), 3.41(m, 2H), 4.52(s, 2H), 5.51(m, 1H), 5.59(d, 1H), 7.58(d, 2H) | 266 | Meth 31 |
| 62 | 5-(3-Dimethylaminoprop-2-en-1-oyl)-1-methyl-2-cyclopropylimidazole | 0.83(m, 2H), 0.94(m, 2H), 1.97(m, 1H), 2.95(br s, 6H), 3.91(s, 3H), 5.55(d, 1H), 7.50(m, 2H) | | Meth 33 |
| 63 | 5-(3-Dimethylaminoprop-2-en-1-oyl)-1-propyl-2-cyclopropylimidazole | 0.80(m, 7H), 1.65(m, 2H), 1.95(m, 1H), 2.95(br s, 6H), 4.40(t, 2H), 5.55(d, 2H), 7.50(m, 2H) | 248 | Meth 35 |
| 64 | 5-(3-Dimethylaminoprop-2-en-1-oyl)-1-isopropyl-2-cyclopropylimidazole | 0.91(m, 4H), 1.49(d, 6H), 2.04(m, 1H), 2.93(m, 6H), 5.51(m, 2H), 7.40(s, 1H), 7.51(d, 1H) | 248 | Meth 37 |
| 65 | 5-(3-Dimethylaminoprop-2-en-1-oyl)-1-ethyl-2-cyclopropylimidazole | 0.88(m, 4H), 1.24(t, 3H), 1.99(m, 1H), 2.94(br s, 6H), 4.47(q, 2H), 5.53(d, 1H), 7.51(m, 2H) | 234 | Meth 39 |
| 66 | 5-(3-Dimethylaminoprop-2-en-1-oyl)-1-propyl-2-methylimidazole | 0.82(t, 3H), 1.60(m, 2H), 2.32(s, 3H), 2.95(br s, 6H), 4.25(t, 2H), 5.58(d, 1H), 7.54(d, 1H), 7.57(s, 1H) | 222 | Meth 41 |
| 67 | 5-(3-Dimethylaminoprop-2-en-1-oyl)-1-isopropylimidazole | 1.43(d, 6H), 2.95(m, 6H), 5.32(m, 1H), 5.58(d, 1H), 7.60(m, 2H), 7.90(s, 1H) | | Meth 43 |

| Meth | Compound | NMR | M/z | SM |
|---|---|---|---|---|
| 68 | 5-(3-Dimethylaminoprop-2-en-1-oyl)-1-propylimidazole | 0.75(t, 3H), 1.65(m, 2H), 2.95(br s, 6H), 4.25(t, 2H), 5.62(d, 1H), 7.55(d, 1H), 7.64(s, 1H), 7.66(s, 1H) | 208 | Meth 49 |

[1] DMF:DMF.DMA(1:1) used as solvent. Purified by flash chromatography on silica gel eluting with DCM/2% methanolic ammonia(100:0 increasing in polarity to 95:5).
[2] DMF.DMA used as solvent
[3] Starting material(2-methyl-4-acetylimidazole) was synthesized according to Tetrahedron letters 1985, 26(29), 3423-3426.

Method 69

2-Anilino-4-(1-isopropyl-2-methoxymethylimidazol-5-yl)pyrimidine 5-(3-Dimethylaminoprop-2-en-1-oyl)-1-isopropyl-2-methoxymethylimidazole (Method 50; 1.26 g, 5 mmol), phenylguanidine hydrogen carbonate (1.09 g, 5.5 mmol) and sodium methoxide (594 mg, 11 mmol) were suspended in anhydrous DMA (10 ml) and the mixture heated at 110° C. for 3 hours. The volatiles were evaporated in vacuo the residues was suspended in water (50 ml). The solution was extracted DCM (3×50 ml). The combined extracts were washed with water (50 ml) and then brine (50 ml), dried and the volatiles removed by evaporation. The residue was purified by flash silica chromatography eluting with DCM:MeOH (100:0 increasing in polarity to 97:3) to give the title compound as brown oil. NMR: 1.43 (d, 6H), 3.30 (s, 3H), 4.56 (s, 2H), 5.54 (m, 1H), 6.96 (t, 1H), 7.05 (d, 1H), 7.24 (t,2H), 7.44 (s, 1H), 7.65 (d, 2H), 8.41 (d, 1H), 9.42 (s, 1H); m/z 324.

Methods 70-84

The following compounds were prepared by the procedure of Method 69.

| Meth | Compound | NMR | M/z | SM |
|---|---|---|---|---|
| 70 | 2-Anilino-4-(1-methyl-2-methoxymethylimidazol-5-yl)pyrimidine | 3.30(s, 3H) 3.99(s, 3H), 4.50(s, 2H), 6.94(t, 1H), 7.13(d, 1H), 7.28(t, 2H), 7.65(s, 1H), 7.69(d, 2H), 8.41(d, 1H), 9.48(s, 1H) | 296 | Meth 51 |
| 71 | 2-Anilino-4-(1-methyl-2-isopropylimidazol-5-yl)pyrimidine | 1.36(d, 6H), 3.08(m, 1H), 3.96(s, 3H), 6.94(d, 1H), 7.05(t, 1H), 7.19(s, 1H), 7.37(t, 2H), 7.53(s, 1H), 7.58(d, 2H), 8.36(d, 1H) | 294 | Meth 53 |
| 72 | 2-Anilino-4-(1-ethyl-2-methoxymethylimidazol-5-yl)pyrimidine | 1.17(t, 3H), 3.28(s, 3H), 4.51(s, 2H), 4.60(q, 2H), 6.97(t, 1H), 7.16(d, 1H), 7.29(t, 2H), 7.64(d, 2H), 7.71(s, 1H), 8.40(d, 1H), 9.40(s, 1H) | 310 | Meth 54 |
| 73 | 2-Anilino-4-(1,2-diethylimidazol-5-yl)pyrimidine | 1.15(t, 3H), 1.27(t, 3H), 2.72(q, 2H), 4.53(q, 2H), 6.96(t, 1H), 7.11(d, 1H), 7.28(t, 2H), 7.64(m, 3H), 8.33(d, 1H), 9.34(s, 1H) | 294 | Meth 55 |
| 74 | 2-Anilino-4-(1,2-dimethylimidazol-5-yl)pyrimidine | 2.37(s, 3H), 3.93(s, 3H), 6.95(t, 1H), 7.08(d, 1H), 7.28(t, 2H), 7.59(s, 1H), 7.69(d, 2H), 8.35(d, 1H), 9.43(s, 1H) | 266 | Meth 57 |
| 75 | 2-Anilino-4-(1-propyl-2-methoxymethylimidazol-5-yl)pyrimidine | (400 MHz), 0.67(t, 3H), 1.53(sext, 2H), 3.30(s, 3H), 4.54(m, 4H), 7.00(t, 1H), 7.15(d, 1H), 7.32(t, 2H), 7.64(d, 2H), 7.70(s, 1H), 8.42(d, 1H), 9.43(s, 1H) | 324 | Meth 58 |
| 76 | 2-Anilino-4-(1-isopropyl-2-isopropylimidazol-5-yl)pyrimidine | 1.23(d, 6H), 1.43(d, 6H), 3.22(m, 1H), 5.61(m, 1H), 6.96(t, 1H), 7.01(d, 1H), 7.26(t, 2H), 7.42(s, 1H), 7.64(d, 2H), 8.38(d, 1H), 9.39(br s, 1H) | 323 | Meth 59 |
| 77 | 2-Anilino-4-(1-ethyl-2-isopropylimidazol-5-yl)pyrimidine | 1.23(t, 3H), 1.38(d, 6H), 3.05(m, 1H), 4.50(q, 2H), 6.94(d, 1H), 7.06(t, 1H), 7.34(t, 2H), 7.56(d, 2H), 7.58(s, 1H), 8.32(d, 1H) | 309 | Meth 60 |

-continued

| Meth | Compound | NMR | M/z | SM |
|---|---|---|---|---|
| 78 | 2-Anilino-4-(1-isopropyl-2-ethoxymethylimidazol-5-yl)pyrimidine | 1.12(t, 3H), 1.46(d, 6H), 3.49(m, 2H), 4.58(s, 2H), 5.54(m, 1H), 6.97(t, 1H), 7.06(d, 1H), 7.28(t, 2H), 7.45(s, 1H), 7.66(d, 2H), 8.42(d, 1H), 9.43(s, 1H) | 338 | Meth 61 |
| 79 | 2-Anilino-4-(1-methyl-2-cyclopropylimidazol-5-yl)pyrimidine | 0.83(m, 2H), 0.94(m, 2H), 2.08(m, 1H), 4.04(s, 3H), 6.93(t, 1H), 7.09(d, 1H), 7.27(t, 2H), 7.51(s, 1H), 7.70(d, 2H), 8.38(d, 1H), 9.40(s, 1H) | 292 | Meth 62 |
| 80 | 2-Anilino-4-(1-propyl-2-cyclopropylimidazol-5-yl)pyrimidine | 0.70(t, 3H), 0.90(m, 4H), 1.55(m, 2H), 2.06(m, 1H), 4.63(t, 2H), 6.93(t, 1H), 7.06(d, 1H), 7.27(t, 2H), 7.56(s, 1H), 7.70(d, 2H), 8.32(d, 1H), 9.35(s, 1H) | 320 | Meth 63 |
| 81 | 2-Anilino-4-(1-isopropyl-2-cyclopropylimidazol-5-yl)pyrimidine | 0.96(m, 4H), 1.53(d, 6H), 2.13(m, 1H), 5.80(m, 1H), 6.99(m, 2H), 7.28(t, 2H), 7.37(s, 1H), 7.67(d, 2H), 8.36(d, 1H), 9.40(s, 1H) | 320 | Meth 64 |
| 82 | 2-Anilino-4-(1-ethyl-2-cyclopropylimidazol-5-yl)pyrimidine | 0.92(m, 4H), 1.23(t, 3H), 2.07(m, 1H), 4.69(q, 2H), 6.98(t, 1H), 7.08(d, 1H), 7.29(t, 2H), 7.57(s, 1H), 7.65(d, 2H), 8.33(d, 1H), 9.33(s, 1H) | 306 | Meth 65 |
| 83 | 2-Anilino-4-(1-propyl-2-methylimidazol-5-yl)pyrimidine | 0.66(t, 3H), 1.51(m, 2H), 2.39(s, 3H), 4.49(t, 2H), 6.99(t, 1H), 7.09(d, 1H), 7.62(s, 1H), 7.65(d, 2H), 8.36(d, 1H), 9.38(s, 1H) | 294 | Meth 66 |
| 84 | 2-Anilino-4-(1-propylimidazol-5-yl)pyrimidine | 0.68(t, 3H), 1.55(m, 2H), 4.48(t, 2H), 6.97(t, 1H), 7.14(d, 1H), 7.30(t, 2H), 7.63(d, 2H), 7.73(s, 1H), 7.88(s, 1H), 8.38(d, 1H), 9.40(s, 1H) | 280 | Meth 68 |

Method 85

2-Amino-4-(1-methoxyisopropyl-2-methoxymethylimidazol-5-yl)pyrimidine 5-(3-Dimethylaminoprop-2-en-1-oyl)-1-methoxyisopropyl-2-methoxymethylimidazole (Method 56; 3.13, 11.1 mmol) and guanidine hydrochloride (2.65 g, 27.8 mmol) were suspended in 1-butanol (20 ml). Sodium methoxide (2.4 g, 44 mmol) was added in one portion and the mixture heated under reflux, under an atmosphere of nitrogen, for 18 hours. The volatiles were removed by evaporation. Water (50 ml) was added and extracted EtOAc (3×50 ml). The organic layers were combined and dried with Chemelut CE1010 and the solvent evaporated in vacuo. The residue was purified by flash silica chromatography eluting with DCM:MeOH (100:0 increasing in polarity to 95:5) to give the title compound as an orange solid (1.86 g, 60%). NMR: 1.43 (d, 3H), 3.16 (s, 3H), 3.24 (s, 3H), 3.63 (m, 1H), 3.89 (m, 1H), 4.50 (q, 2H), 5.26 (m, 1H), 6.57 (s, 2H), 6.80 (d, 1H), 7.40 (s, 1H), 8.21 (d, 1H); m/z 278.

Methods 86-88

The following compounds were prepared by the procedure of Method 85.

| Meth | Compound | NMR | M/z | SM |
|---|---|---|---|---|
| 86 | 2-Amino-4-(1-methyl-2-ethylimidazol-5-yl)pyrimidine | 1.21(t, 3H), 2.69(q, 2H), 3.92(s, 3H), 6.52(brs, 2H), 6.81(d, 1H), 7.48(s, 1H), 8.15(d, 1H) | 203 | Meth 52 |
| 87 | 2-Amino-4-(1-propyl-2-methylimidazol-5-yl)pyrimidine | 0.82(t, 3H), 1.59(q, 2H), 2.38(s, 3H), 4.42(t, 2H), 6.45(s, 2H), 6.82(d, 1H), 7.50(s, 1H), 8.20(d, 1H) | 218 | Meth 66 |
| 88 | 2-Amino-4-(1-isopropylimidazol-5-yl)pyrimidine | 1.53(d, 6H), 5.05(s, 2H), 5.59(sept, 1H), 6.85(d, 1H), 7.56(s, 1H), 7.78(s, 1H), 8.23(d, 1H) | 204 | Meth 67 |

Method 89

2-Anilino-4-(1-methyl-2-n-butylimidazol-5-yl)pyrimidine

2-Anilino-4-(1,2-dimethylimidazol-5-yl)pyrimidine (Method 74; 2 g, 7.55 mmol) was dissolved in anhydrous THF (100 ml) at RT under a nitrogen atmosphere. The stirring solution was cooled using dry-ice/acetone bath to −70° C. A 1.6M solution of n-butyl lithium in hexane (6.3 ml, 10.08 mmol) was added drop-wise keeping temperature <−60° C. until the dark red colour remained. One more equivalent of n-butyl lithium in hexane (4.7 ml, 7.55 mmol), was then added dropwise keeping the temperature below −60° C. At this point the solution stirred at −70° C. for 10 minutes when propyl iodide (809 μl, 8.29 mmol) was added, the temperature was maintained at −70° C. for an additional 10 minutes then allowed to rise to RT. The reaction was allowed to stir for 1 hr at room temperature when water (100 ml) was added. The aqueous layer extracted with EtOAc (2×20 ml). Organics were combined, dried solvent evaporated in vacuo. The residue was purified by flash silica chromatography DCM: MeOH (95:5) to yield the title compound (1.03 g, 45%) as a pure white solid NMR: 0.90 (t, 3H), 1.39 (m, 2H), 1.66 (m, 2H), 2.70 (t, 2H), 3.94 (s, 3H), 6.95 (t, 1H), 7.08 (d, 1H), 7.28 (t, 2H, 7.65 (d, 2H), 7.59 (s, 1H), 8.35 (d, 1H), 9.42 (s, 1H); m/z 308.

Methods 90-102

The following compounds were prepared by the procedure of Method 89.

| Meth | Compound | NMR | M/z | SM |
|---|---|---|---|---|
| 90 | 2-Anilino-4-[1-methyl-2-(2-hydroxy-3,3-dimethylbutyl)imidazol-5-yl]pyrimidine | 0.9(s, 3H), 2.65(m, 1H), 2.84(m, 1H), 3.60(m, 1H), 3.98(s, 3H), 4.83(d, 1H), 6.97(t, 1H), 7.10(d, 1H), 7.28(dd, 2H), 7.63(s, 1H), 7.71(d, 2H), 8.38(d, 1H), 9.45(d, 1H) | 352 | Pivaldehyde |
| 91 | 2-Anilino-4-(1-methyl-2-propylimidazol-5-yl)pyrimidine | 0.95(t, 3H), 1.70(m, 2H), 2.68(t, 2H), 3.92(s, 3H), 6.95(t, 1H), 7.08(d, 1H), 7.28(t, 2H), 7.60(s, 1H), 7.69(d, 2H), 8.34(d, 1H), 9.44(s, 1H) | 294 | Ethyl Iodide + Meth 74 |
| 92 | 2-Anilino-4-[1-methyl-2-(2-methoxyethyl)imidazol-5-yl]pyrimidine | 2.96(t, 2H), 3.26(s, 3H), 3.70(t, 2H), 3.95(s, 3H), 6.94(t, 1H), 7.09(d, 1H), 7.26(t, 2H), 7.60(s, 1H), 7.74(d, 2H), 8.38(s, 1H), 9.44(s, 1H) | 309 | Chloromethyl-methylether + Meth 74 |
| 93 | 2-Anilino-4-(1-ethyl-2-propylimidazol-5-yl)pyrimidine | 0.96(t, 3H), 1.15(t, 3H), 1.70(m, 2H), 2.68(t, 2H), 4.54(q, 2H), 6.97(t, 1H), 7.10(d, 1H), 7.29(t, 2H), 7.65(m, 3H), 8.34(d, 1H), 9.35(s, 1H) | 308 | Ethyl Iodide + Ex 28 WO 02/20512 |
| 94 | 2-Anilino-4-(1-ethyl-2-butylimidazol-5-yl)pyrimidine | 0.92(t, 3H), 1.14(t, 3H), 1.38(m, 2H), 1.68(m, 2H), 2.70(t, 2H), 4.56(q, 2H), 6.98(t, 1H), 7.08(d, 1H), 7.26(t, 2H), 7.64(m, 3H), 8.37(d, 1H), 9.36(s, 1H) | 322 | Propyl Iodide + Ex 28 WO 02/20512 |
| 95 | 2-Anilino-4-(1-isopropyl-2-propylimidazol-5-yl)pyrimidine | 1.98(t, 3H), 1.4(d, 6H), 1.78(m, 2H), 2.76(t, 2H), 5.62(m, 1H), 6.97(t, 1H), 7.02(d, 1H), 7.30(t, 2H), 7.44(s, 1H), 7.66(d, 2H), 8.39(d, 1H), 9.40(s, 1H) | 322 | Ethyl Iodide + Ex 32 WO 02/20512 |
| 96 | 2-Anilino-4-(1-isopropyl-2-ethylimidazol-5-yl)pyrimidine | 1.26(t, 3H), 1.44(d, 6H), 2.80(q, 2H), 5.62(m, 1H), 6.97(t, 1H), 7.02(d, 1H), 7.26(t, 2H), 7.42(s, 1H), 7.64(s, 2H), 8.39(d, 1H), 9.39(s, 1H) | 308 | Methyl Iodide + Ex 32 WO 02/20512 |
| 97 | 2-Anilino-4-(1-methyl-2-(2-methyl-2-hydroxypropyl)imidazol-5-yl)pyrimidine | No NMR data | 324 | Acetone + Ex 5 WO 02/20512 |
| 98 | 2-{4-[N-(2-methoxyethyl)-N-(t-butyl)sulphamoyl]anilino}-4-(1-ethyl-2-(2-methyl-2-hydroxypropyl)imidazol-5-yl)pyrimidine | 1.22-1.10(m, 18H), 2.82(s, 2H), 3.28(s, 3H), 3.55-3.42(m, 4H), 4.79(q, 2H), 4.94(s, 1H), 7.22(d, 1H), 7.75-7.70(m, 3H), 7.88(d, 2H), 8.42(d, 1H), 9.88(s, 1H). | 531 | Acetone + Meth 107 |
| 99 | 2-Anilino-4-(1,2-dipropyl-imidazol-5-yl)pyrimidine | No NMR data | 322 | Ethyl iodide + Meth 83 |

-continued

| Meth | Compound | NMR | M/z | SM |
|---|---|---|---|---|
| 100 | 4-(2-But-3-enyl-1-propylimidazol-5-yl)-2-{4-[N-(2-methoxyethyl)-N-(2-trimethylsilylethoxymethyl), sulphamoyl]anilino}pyrimidine | No NMR data | 601 | Allyl bromide + Meth 108 |
| 101[1] | 4-[2-(3,3-Dimethyl-2-hydroxybut-1-yl)-1-(propyl)imidazol-5-yl]-2-anilinopyrimidine | 0.64(t, 3H), 0.97(s, 9H), 1.58-1.42(m, 2H), 3.59(s, 1H), 4.52-4.41(m, 1H), 4.63-4.58(m, 1H), 4.90(s, 1H), 6.99(t, 1H), 7.10(d, 1H), 7.30(t, 2H), 7.63-7.60(m, 3H), 8.39(d, 2H), 9.39(s, 1H). | 380 | Pivaldehyde + Meth 83 |
| 102[1] | 4-{2-[2-(4-Chlorophenyl)ethyl]-1-(methyl)imidazol-5-yl}-2-anilinopyrimidine | 3.02(s, 4H), 3.90(s, 3H), 6.97(t, 1H), 7.09(d, 1H), 7.30(m, 6H), 7.64(s, 1H), 7.70(d, 2H), 8.38(d, 1H), 9.42(s, 1H) | 390 | 4-chlorobenzyl bromide + Meth 74 |

[1]Purified by chromatography on silica eluting with 2% MeOH/EtOAc

Method 103

2-Anilino-4-(1-methyl-2-(3,3-dimethylbut-1-enylimidazol-5-yl)pyrimidine

2-Anilino-4-[1-methyl-2-(2-hydroxy-3,3-dimethylbutyl)imidazol-5-yl]pyrimidine (Method 90; 988 mg, 2.8 mmol) was dissolved in DCM (20 ml). To this was added triethylamine (1.18 ml, 8.4 mmol) followed by methanesulphonyl chloride (458 µl, 5.92 mmol) in portions. After 18 hr the volatiles were evaporated in vacuo and the residue resuspended in toluene (20 ml). To this stirred solution was added 1,8-diazabicyclo[5.4.0]undec-7-ene(4 ml, 26.7 mmol) and heated to reflux for 1 hr. Volatiles evaporated in vacuo and the residue was triturated with water. The resultant solid was collected by filtration, washed water (20 ml) and dried under vacuum at 60° C. to yield the title compound (830 mg, 90%). NMR 1.15 (s, 9H), 4.04 (s, 3H), 6.38 (d, 1H), 6.8 (d, 1H), 6.96 (t, 1H), 7.12 (d, 1H), 7.28 (t, 2H), 7.71 (m, 3H), 8.38 (d, 1H), 9.48 (s, 1H); m/z 334.

Method 104

2-Anilino-4-[1-methyl-2-(3,3-dimethylbutylimidazol-5-yl]pyrimidine

To a solution of 2-anilino-4-(1-methyl-2-(3,3-dimethylbut-1-enylimidazol-5-yl)pyrimidine (Method 103; 200 mg, 0.6 mmol) in EtOH (20 ml) was added 10% Pd/C (100 mg) and stirred under a hydrogen atmosphere for 3 days. The reaction mixture was passed through a pad of celite to remove the catalyst and the filtrate evaporated in vacuo. The residue was triturated with ether to give the title compound 105 mg (53%). NMR 0.97 (s, 9H), 1.60 (m, 2H), 2.67 (m, 2H), 3.97 (s, 3H), 6.98 (t, 1H), 7.08 (d, 1H), 7.27 (dd, 2H), 7.60 (s, 1H), 7.70 (d, 2H), 8.39 (d, 1H), 9.42 (s, 1H); m/z 336.

Method 105

4-(2-Formyl-1-isopropylimidazol-5-yl)-2-{4-[N-(2-methoxyethyl)-N-(2-trimethylsilylethoxymethyl) sulphamoyl]anilino}pyrimidine 4-(1-Isopropylimidazol-5-yl)-2-{4-[N-(2-methoxyethyl)-N-(2-trimethylsilylethoxymethyl)sulphamoyl] anilino}pyrimidine (Method 106; 1.22 g, 2.33 mmol), was dissolved in anhydrous THF (70 ml), under nitrogen. The solution was cooled to −78° C. and n-butyl lithium (3.48 ml of a 1.6 N solution in hexanes, 5.57 mmol), was added slowly, maintaining the temperature at less than −65° C. The reaction mixture was then stirred at −78° C. for 30 minutes, then DMF (345 µl, 4.46 mmol), was added and mixture allowed to warm to ambient temperature and stirred for 1 hour. The reaction mixture was then poured into water (100 ml), and extracted with EtOAc (2×50 ml). The organic extracts were combined, washed with water (50 ml), brine (50 ml), and dried. The volatiles were removed and the residue was purified by chromatography on silica gel eluting with 3% MeOH in DCM, to give the title product, (307 mg, 24%), as a pale yellow foam. NMR: 0.02 (s, 9H), 0.83 (dd, 2H), 1.63 (d, 6H), 3.28 (s, 3H), 3.37 (t, 2H), 3.42 (dd, 2H), 3.52 (t, 2H), 4.78 (s, 2H), 5.71 (m, 1H), 7.40 (d, 1H), 7.82 (d, 2H), 7.92 (s, 1H), 8.01 (d, 2H), 8.78 (d, 1H), 9.91 (s, 1H); m/z: 573 [MH]−.

Method 106

4-(1-Isopropylimidazol-5-yl)-2-{4-[N-(2-methoxyethyl)-N-(2-trimethylsilylethoxymethyl) sulphamoyl] anilino}pyrimidine Sodium t-butoxide (1.42 g, 14.78 mmol), was added to a stirred solution of 2-amino-4-(1-isopropylimidazol-5-yl)pyrimidine (Method 88; 2.0 g, 9.85 mmol), N-(2-methoxyethyl)-N-(2-trimethylsilylethoxymethyl-4-iodobenzene-sulphonamide (Method 112; 5.11 g, 10.84 mmol), tris (dibenzylideneacetone), dipalladium (0), (650 mg, 0.71 mmol), and 2,2'-bis(diphenylphosphino)-1,1'-binaphthyl (470 mg, 0.75 mmol), in dioxane (180 ml), and the mixture heated at 80° C. overnight. The reaction was cooled to ambient temperature and acetic acid (282 µl, 4.93 mmol), added. The reaction mixture was poured into water (70 ml), and extracted with EtOAc (3×40 ml). The organic extracts were combined, washed with water (2×40 ml), saturated brine (40 ml), dried, and the solvent removed by evaporation. The residue was purified by flash chromatography on silica gel eluting with DCM/MeOH (97:3), and then by chromatography on silica gel eluting with DCM/MeOH (98.5:1.5), to yield the title compound (1.95 g, 36%). NMR: 0.01 (s, 9H), 085 (dd, 2H), 1.53 (d, 6H), 3.26 (s, 2H), 3.37 (t, 2H), 3.44 (dd, 2H), 3.52 (t, 1H), 4.79 (s, 2H), 5.57 (m, 1H), 7.36 (d, 1H), 8.80 (m, 3H), 7.98 (d, 2H), 8.19 (s, 1H), 8.58 (d, 1H), 10.13 (s, 1H); m/z: 545 [MH]−.

Methods 107-108

The following compounds were prepared by an analogous procedure to Method 106.

| Meth | Compound | NMR | M/z | SM |
|---|---|---|---|---|
| 107 | 4-(1-Ethyl-2-methylimidazol-5-yl)-2-{4-[N-(2-methoxyethyl)-N-t-butylsulphamoyl]anilino}pyrimidine | 1.15-1.22(m, 12H), 2.40(s, 3H), 3.24-3.28(m, 3H), 3.46-3.55(m, 4H), 4.59(q, 2H), 7.20(d, 1H), 7.68(s, 1H), 7.70(d, 2H), 7.89(d, 2H), 8.42(d, 1H), 9.84(s, 1H) | 473 | Meth 27 WO 02/20512 + Meth 113 |
| 108 | 4-(2-Methyl-1-propylimidazol-5-yl)-2-{4-[N-(2-methoxyethyl)-N-(2-trimethylsilylethoxymethyl), sulphamoyl]anilino}pyrimidine | No NMR data | 559 [MH]$^-$ | Meth 87 + Meth 112 |

Method 109

4-(1-Methyl-2-(2-methylpropyl)imidazol-5-yl)-2-anilinopyrimidine 4-(1-Methyl-2-(2-methylprop-1-enyl)imidazol-5-yl)-2-anilinopyrimidine (method 110; 400 mg, 1.3 mmol), and 10% Pd on C catalyst (150 mg), in ethanol (50 ml), was hydrogenated at 40 C and 20 bar for 18 hours. The catalyst was removed by filtration and the filter pad washed with ethanol. The solvent was evaporated and the residue triturated with ether and collected by filtration to give the title compound (280 mg, 71%). M/z: 308.

Method 110

4-(1-Methyl-2-(2-methylprop-1-enyl)imidazol-5-yl)-2-anilinopyrimidine

Methanesulphonyl chloride (151 µl, 1.96 mmol), was added to a solution of 2-anilino-4-(1-methyl-2-(2-methyl-2-hydroxypropyl)imidazol-5-yl)pyrimidine (Method 97; 600 mg, 1.86 mmol), and triethylamine (777 µl, 5.58 mmol), in DCM (10 ml), at ambient temperature under nitrogen. The mixture was stirred for 3 hours then adsorbed directly onto silica gel and purified by chromatography eluting with EtOAc to give the title compound (235 mg, 42%). NMR: 1.98 (s, 3H), 2.14 (s, 3H), 3.99 (s, 3H), 6.24 (s, 1H), 6.98 (t, 1H), 7.10 (d, 1H), 7.28 (dd, 2H), 7.69-7.72 (m, 3H), 8.40 (d, 1H), 9.42 (s, 1H); m/z: 306.

Method 111

The following compounds were prepared by an analogous procedure to Method 110.

| Meth | Compound | M/z | SM |
|---|---|---|---|
| 111 | 4-[2-(2-Methylprop-1-enyl)-1-ethylimidazol-5-yl]-2-{4-[N-(2-methoxyethyl)-N-t-butylsulphamoyl]anilino}pyrimidine | 513 | Meth 98 |

Method 112

N-(2-Methoxyethyl)-N-(2-trimethylsilylethoxymethyl)-4-iodobenzenesulphonamide Sodium hydride (2.2 g, 55 mmol), was added to a solution of N-(2-methoxyethyl)-4-iodobenzenesulphonamide (Method 4; 15.8 g, 46.3 mmol), in DMF (250 ml), under nitrogen at 0° C. and the mixture stirred for 1 hour. 2-Trimethylsilylethoxymethyl chloride (10 g, 60 mmol), was added and the mixture stirred overnight at ambient temperature. The volatiles were removed by evaporation and the residue dissolved in ether, washed with water and then brine, dried (Na$_2$SO$_4$), and the solvent evaporated to give the title compound (22.6 g, 74%). NMR: 0.2 (s, 9H), 0.89 (t, 2H), 3.30 (s, 3H), 3.40-3.36 (m, 2H), 3.59-3.43 (m, 2H), 4.82 (s, 2H), 7.60 (d, 2H), 7.84 (d, 2H).

Method 113

N-(2-Methoxyethyl)-N-(t-butyl)-4-iodobenzenesulphonamide

Sodium hydride (71 mg, 1.77 mg), was added to a solution of N-t-butyl-4-iodobenzenesulphonamide (Method 5; 500 mg, 1.47 mmol), in anhydrous DMF (15 ml), under nitrogen at 0° C. The resulting suspension was stirred at 0° C. for 30 minutes. A solution of 1-bromo-2-methoxyethane (167 µl, 1.77 mmol), and sodium iodide (265 mg, 1.77 mmol), in DMF (15 ml), (pre-stirred at ambient temperature for 1 hr), was then added dropwise to the mixture while the, reaction temperature was maintained at 0° C. and the mixture stirred for 10 minutes. The mixture was allowed to warm to ambient temperature, and then heated at 60° C. for 20 hours. A further solution of 1-bromo-2-methoxyethane (167 µl, 1.77 mmol), and sodium iodide (265 mg, 1.77 mmol), in DMF (15 ml), (pre-stirred at ambient temperature for 1 hr), was then added dropwise to the mixture at ambient temperature and the reaction mixture was heated at 60° C. for 20 hours. The mixture was cooled and solvent removed by evaporation. The residue was dissolved in ether (25 ml), washed with 10% aqueous sodium hydroxide solution (20 ml), water (3×25 ml), and dried. The volatiles were removed by evaporation and the residue purified by flash chromatography on silica gel eluting with DCM to yield the title product as a clear oil that crystallised on standing (147 mg, 25%), NMR: 1.23 (s, 9H), 3.24 (s, 3H), 3.48 (s, 4H), 7.57 (d, 2H), 7.94 (d, 2H).

Method 114

4-[2-(3,3-Dimethylbut-1-en-1-yl)-1-(propyl)imidazol-5-yl]-2-anilinopyrimidine Triethylamine (0.74 ml, 5.05 mmol), followed by methane sulphonyl chloride (0.103 ml, 1.33 mmol) was added to a stirred solution of 4-[2-(3,3-dimethyl-2-hydroxybut-1-yl)-1-(propyl)imidazol-5-yl]-2-anilinopyrimidine (Method 101; 480 mg, 1.26 mmol) in DCM (40 ml) at ambient temperature and the mixture stirred for 24 hours. The volatiles were removed by evaporation and toluene (10 ml), and 1,8-diazabicyclo[5.4.0]undec-7-ene (0.38 ml, 2.54 mmol) was added to the residue. The mixture was heated at reflux for 5 hours, allowed to cool, washed with water and extracted with EtOAc. The extracts were combined, dried and the solvent removed by evaporation to give the title compound (240 mg, 53%). NMR: 0.64 (t, 3H), 1.15 (s, 9H), 1.53 (q, 2H), 4.64 (t, 2H), 6.38 (d, 1H), 6.80 (d, 1H), 6.99 (t, 1H), 7.10 (d, 1H), 7.28 (t, 2H), 7.62 (d, 3H), 7.75 (s, 1H), 8.38 (d, 1H), 9.38 (s, 1H); m/z 362.

Method 115

4-[2-(3,3-Dimethylbutyl)-1-(propyl)imidazol-5-yl]-2-anilinopyrimidine

A mixture of 10% palladium on charcoal catalyst (100 mg), 4-[2-(3,3-dimethylbut-1-en-1-yl)-1-(propyl)imidazol-5-yl]-2-anilinopyrimidine (Method 114; 230 mg, 0.64 mmol) in ethanol (50 ml) was stirred under an atmosphere of hydrogen for 72 hours. The catalyst was removed by filtration through diatomaceous earth, and the filter pad washed with warm MeOH. The solvent removed by evaporation to give the title compound (200 mg, 86%). M/z 364.

Method 116

4-[2-(Chloromethyl)-1-(propyl)imidazol-5-yl]-2-{4-[N-(2-ethoxyethyl)sulphamoyl]anilino}pyrimidine Chlorosulphonic acid (2.29 g, 20 mmol) was added dropwise to a stirred solution of 2-anilino-4-(1-propyl-2-methoxymethylimidazol-5-yl)pyrimidine (Method 75; 1.29 g, 4.0 mmol) in thionyl chloride (30 ml), cooled to 0-4° C. The solution was allowed to warm to ambient temperature and was then heated under reflux for 18 hour. The mixture was cooled and an oil separated out. The excess thionyl chloride was decanted from this oil, and the residue was washed with thionyl chloride (10 ml) and any volatiles removed by evaporation. The residue was dissolved in MeOH (15 ml), cooled to 0-4° C. and a solution of 2-ethoxyethylamine (3.56 g, 40 mmol) in cold MeOH (15 ml) was added. The reaction mixture was allowed to warm to ambient temperature and stirred for one hour. The mixture was allowed to stand and cooled to 0-4° C. The resulting crystalline product was collected by filtration, washed with MeOH and dried to give the title compound (587 mg, 31%). NMR: 0.70 (t, 3H), 1.05 (t, 3H), 1.55 (m, 2H), 2.86 (m, 2H), 3.33 (m, 4H), 4.60 (t, 2H), 4.95 (s, 2H), 7.25 (d, 1H), 7.46 (t, 1H), 7.71 (d, 2H), 7.75 (s, 1H), 7.86 (d, 2H), 8.50 (d, 1H), 9.90 (s, 1H); m/z 479.

Method 117

4-{2-[2-(4-Chlorophenyl)ethyl]-1-(methyl)imidazol-5-yl}-2-{4-[N-(2-methoxyethyl) sulphamoyl]anilino}pyrimidine 4-{2-[2-(4-Chlorophenyl)ethyl]-1-(methyl)imidazol-5-yl}-2-anilinopyrimidine (Method 102) was treated with 2-methoxyethylamine by the conditions described in Method 116. The crude product was purified by chromatography on silica gel eluting with DCM/MeOH (98:2) to give the title compound (164 mg, 48%) as glassy solid. NMR: 2.88 (q, 2H), 3.02 (s, 4H), 3.15 (s, 3H), 3.26 (m, 2H), 3.92 (s, 3H), 7.21 (d, 1H), 7.32 (d, 4H), 7.44 (s, 1H), 7.66 (s, 1H), 7.68 (d, 2H), 7.90 (d, 2H), 8.44 (d, 1H), 9.92 (s, 1H); m/z 528.

Method 118

2-Anilino-4-(2-formyl-1-propylimidazol-5-yl)pyrimidine

2-Anilino-4-(1-propylimidazol-5-yl)pyrimidine (Method 84) was treated as described in Method 105. The crude product was purified by chromatography on silica gel eluting with EA/IsoHex (80:20) to give the title compound (1.051 g, 48%) as a yellow solid. NMR: 0.63 (t, 3H), 1.59 (m, 2H), 4.94 (t, 2H), 7.01 (t, 1H), 7.30 (m, 3H), 7.63 (d, 2H), 8.0 (s, 1H), 8.55 (d, 1H), 9.60 (s, 1H), 9.80 (s, 1H).

Method 119

2-Anilino-4-(2-dimethylaminomethyl-1-propylimidazol-5-yl)pyrimidine

A mixture of 2-anilino 4-(2-formyl-1-propylimidazol-5-yl)pyrimidine (Method 118; 200 mg, 0.65 mmol) and dimethylamine (391 μl of 2M solution in THF, 0.78 mmol) in MeOH (6 ml) stirred for 3 hours at ambient temperature. Acetic acid (41 mg, 0.716 mmol) and sodium cyanoborohydride (45 mg, 0.716 mmol) were added and the mixture stirred for a further 18 hours. The volatiles were removed by evaporation and residue dissolved in EtOAc (7 ml). This solution was washed with saturated aqueous sodium hydrogen carbonate solution, water, and brine, then dried and the solvent removed by evaporation to give the title compound (210 mg, 96%) as a yellow foam. NMR: 0.62 (t, 6H), 1.50 (m, 2H), 2.23 (s, 6H), 3.60 (s, 2H), 4.56 (m, 2H), 6.98 (t, 1H), 7.10 (d, 1H), 7.28 (t, 2H), 7.62 (m, 3H), 8.39 (d, 1H), 9.39 (s, 1H); m/z 337.

Method 120

2-Anilino 4-(2-ethylamniomethyl-1-propylimidazol-5-yl)pyrimidine

2-Anilino 4-(2-formyl-1-propylimidazol-5-yl)pyrimidine (Method 118) was treated with ethylamine (2M solution in MeOH) by the procedure of Method 119 to give the title compound (185 mg, 93%) as a yellow foam. M/z 337.

Example 87

The following illustrate representative pharmaceutical dosage forms containing the compound of formula (I), or a pharmaceutically acceptable salt or in vivo hydrolysable ester thereof (hereafter compound X), for therapeutic or prophylactic use in humans:—

| (a): Tablet I | mg/tablet |
|---|---|
| Compound X | 100 |
| Lactose Ph•Eur | 182.75 |
| Croscarmellose sodium | 12.0 |
| Maize starch paste (5% w/v paste) | 2.25 |
| Magnesium stearate | 3.0 |

| (b): Tablet II | mg/tablet |
|---|---|
| Compound X | 50 |
| Lactose Ph•Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c): Tablet III | mg/tablet |
|---|---|
| Compound X | 1.0 |
| Lactose Ph•Eur | 93.25 |
| Croscarmellose sodium | 4.0 |
| Maize starch paste (5% w/v paste) | 0.75 |
| Magnesium stearate | 1.0 |

| (d): Capsule | mg/capsule |
|---|---|
| Compound X | 10 |
| Lactose Ph•Eur | 488.5 |
| Magnesium stearate | 1.5 |

| (e): Injection I | (50 mg/ml) |
|---|---|
| Compound X | 5.0% w/v |
| 1M Sodium hydroxide solution | 15.0% v/v |
| 0.1M Hydrochloric acid | (to adjust pH to 7.6) |
| Polyethylene glycol 400 | 4.5% w/v |
| Water for injection | to 100% |

| (f): Injection II | 10 mg/ml |
|---|---|
| Compound X | 1.0% w/v |
| Sodium phosphate BP | 3.6% w/v |
| 0.1M Sodium hydroxide solution | 15.0% v/v |
| Water for injection | to 100% |

| (g): Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

Note

The above formulations may be obtained by conventional procedures well known in the pharmaceutical art. The tablets (a)-(c) may be enteric coated by conventional means, for example to provide a coating of cellulose acetate phthalate.

What is claimed is:

1. A compound of formula (I):

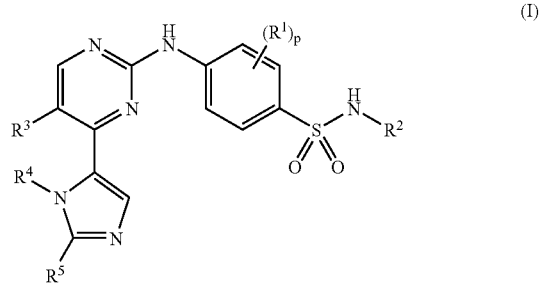

wherein:

$R^1$ is halo, cyano, $C_{1-3}$alkyl or $C_{1-3}$alkoxy;

p is 0-2; wherein the values of $R^1$ may be the same or different;

$R^2$ is $C_{1-4}$alkyl, $C_{2-4}$alkenyl, $C_{2-4}$alkynyl, $C_{3-6}$cycloalkyl, $C_{3-6}$cycloalkyl$C_{1-3}$alkyl, a heterocyclyl or heterocyclyl$C_{1-3}$ alkyl; wherein $R_2$ may be optionally substituted on carbon by one or more methyl, ethyl, methoxy, ethoxy, propoxy, trifluoromethyl, trifluoromethoxy, 2,2,2-trifluoroethoxy or cyclopropylmethoxy; and wherein if said heterocyclyl contains an —NH— moiety that nitrogen may be optionally substituted by one or more methyl, ethyl, acetyl, 2,2,2-trifluoroethyl or methoxyethyl;

$R^3$ is hydrogen, halo or cyano;

$R^4$ is $C_{1-6}$alkyl or $C_{1-6}$alkoxy$C_{1-6}$alkyl;

$R^5$ is substituted methyl, optionally substituted $C_{2-6}$alkyl, or optionally substituted $C_{2-6}$alkenyl; wherein said substituents are selected from one or more methoxy, ethoxy, propoxy, trifluoromethyl, trifluoromethoxy, 2,2,2-trifluoroethoxy or cyclopropylmethoxy;

or a pharmaceutically acceptable salt thereof;

provided that the compound is not 4-(1-methyl-2-ethylimidazol-5-yl)-2-{4-[N-(tetrahydrofur-2-ylmethyl)sulphamoyl]anilino}pyrimidine; 4-(1-methyl-2-ethyl-imidazol-5-yl)-2-{4-[N-(2-methoxyethyl)sulphamoyl]anilino}pyrimidine; 4-(1-methyl-2-isopropyl-imidazol-5-yl)-2-{4-[N-(2-methoxyethyl)sulphamoyl]anilino}pyrimidine; 4-(1-methyl-2-isopropyl-imidazol-5-yl)-2-{4-[N-(cyclopropylmethyl) sulphamoyl]anilino}pyrimidine; 4-(1-methyl-2-isopropyl-imidazol-5-yl )-2-{4-[N-(tetrahydrofur-2-ylmethyl)sulphamoyl]anilino}pyrimidine; 4-(1-methyl-2-ethylimidazol-5-yl)-2-{4-[N-(cyclopropylmethyl)

sulphamoyl]anilino}pyrimidine; 4-(1-methyl-2-ethyl-imidazol-5-yl)-2-[4-(N-cyclopropylsulphamoyl) anilino]pyrimidine; 4-(1-methyl-2-ethylimidazol-5-yl)-2-[4-(N-cyclobutyl-sulphamoyl) anilino]pyrimidine; or 4-(1-methyl-2-methoxymethylimidazol-5-yl)-2-{4-[N-(2-methoxyethyl) sulphamoyl]anilino}pyrimidine.

2. A compound of formula (I) according to claim 1 wherein p is 0; or a pharmaceutically acceptable salt thereof.

3. A compound of formula (I) according to claim 1 wherein $R^2$ is $C_{1-4}$alkyl, $C_{2-4}$alkenyl, $C_{3-6}$cycloalkyl, $C_{3-6}$cycloalkyl$C_{1-3}$alkyl or heterocyclyl$C_{1-3}$alkyl; wherein $R^2$ may be optionally substituted on carbon by one or more methoxy, ethoxy or trifluoromethyl; or a pharmaceutically acceptable salt thereof.

4. A compound of formula (I) according to claim 1 wherein $R^3$ is hydrogen; or a pharmaceutically acceptable salt thereof.

5. The compound of formula (I) according to claim 1 wherein $R^4$ is $C_{1-4}$alkyl or $C_{1-4}$alkoxy$C_{1-4}$alkyl; or a pharmaceutically acceptable salt thereof.

6. The compound of formula (I) according to claim 1 wherein $R^5$ is substituted methyl, or optionally substituted $C_{2-6}$alkyl; wherein said substituents are selected from one or more methoxy; or a pharmaceutically acceptable salt thereof.

7. A compound of formula (I) as depicted in claim 1 wherein:
   p is 0;
   $R^2$ is 2-ethoxyethyl, 2-methoxyethyl, 2,2,2-trifluoroethyl, 3-methoxypropyl, t-butyl, allyl, cyclopropyl, cyclobutyl, cyclopropylmethyl or tetrahydrofur-2-ylmethyl;
   $R^3$ is hydrogen;
   $R^4$ is methyl, ethyl, isopropyl or 1-methoxyprop-2-yl; or
   $R^5$ is methoxymethyl, isopropyl, ethyl, butyl or 3,3-dimethylbutyl;
or a pharmaceutically acceptable salt thereof;
provided that the compound is not 4-(1-methyl-2-ethylimidazol-5-yl)-2-{4-[N-(tetrahydrofur-2-ylmethyl)sulphamoyl] anilino}pyrimidine; 4-(1-methyl-2-ethyl-imidazol-5-yl)-2-{4-[N-(2-methoxyethyl)sulphamoyl]anilino}pyrimidine; 4-(1-methyl-2-isopropyl-imidazol-5-yl)-2-{4-[N-(2-methoxyethyl)sulphamoyl]anilino}pyrimidine; 4-(1-methyl-2-isopropyl-imidazol-5-yl)-2-{4-[N-(cyclopropylmethyl)sulphamoyl]anilino}pyrimidine; 4-(1-methyl-2-isopropyl-imidazol-5-yl)-2-{4-[N-(tetrahydrofur-2-ylmethyl)sulphamoyl]anilino}pyrimidine; 4-(1-methyl-2-ethylimidazol-5-yl)-2-{4-[N-(cyclopropylmethyl)sulphamoyl]anilino}pyrimidine; 4-(1-methyl-2-ethyl-imidazol-5-yl)-2-[4-(N-cyclopropylsulphamoyl)anilino] pyrimidine; 4-(1-methyl-2-ethylimidazol-5-yl)-2-[4-(N-cyclobutyl-sulphamoyl)anilino]pyrimidine; or 4-(1-methyl-2-methoxymethylimidazol-5-yl)-2-{4-[N-(2-methoxyethyl) sulphamoyl]anilino}pyrimidine.

8. A compound of formula (I) as depicted in claim 1 selected from:
   4-(1,2-diethylimidazol-5-yl)-2-{4-[N-(2-ethoxyethyl)sulphamoyl]anilino}pyrimidine;
   4-(1,2-diethylimidazol-5-yl)-2-{4-[N-(cyclopropyl)sulphamoyl]anilino}pyrimidine; and
   4-(1,2-diethylimidazol-5-yl)-2-{4-[N-(allyl)sulphamoyl] anilino}pyrimidine;
or a pharmaceutically acceptable salt thereof.

9. A process for preparing a compound of formula (I) or a pharmaceutically acceptable salt thereof as claimed in claim 1, which process (wherein $R^1, R^2, R^3, R^4, R^5$ and p are, unless otherwise specified, as defined in claim 1) comprises of:
Process a) reaction of a pyrimidine of formula (II):

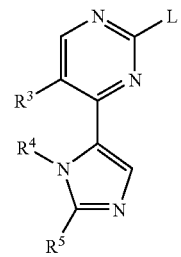

(II)

wherein L is a displaceable group; with an aniline of formula (III):

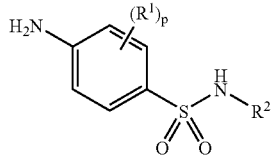

(III)

Process b) reacting a compound of formula (IV):

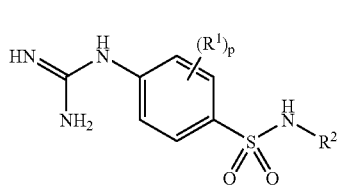

(IV)

with a compound of formula (V):

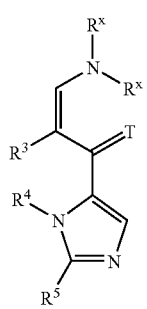

(V)

wherein T is O or S; $R^x$ may be the same or different and is $C_{1-6}$alkyl;

Process c) reacting a pyrimidine of formula (VI):

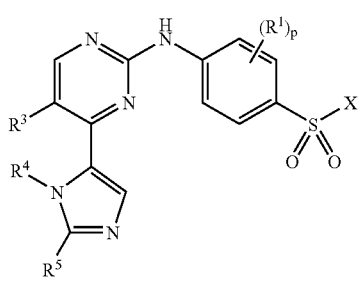
(VI)

wherein X is a displaceable group; with an amine of formula (VII):

R²—NH₂     (VII)

or
Process d) reacting a pyrimidine of formula (VIII)

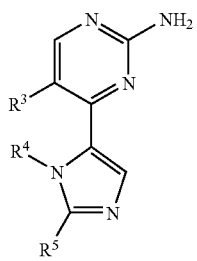
(VIII)

with a compound of formula (IX):

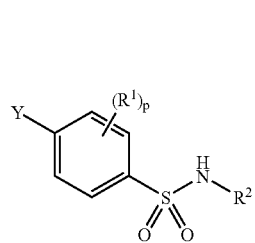
(IX)

where Y is a displaceable group;
and thereafter if necessary:

i) converting a compound of the formula (I) into another compound of the formula (I);
ii) removing any protecting groups;
iii) forming a pharmaceutically acceptable salt.

10. A pharmaceutical composition which comprises a compound of the formula (I), or a pharmaceutically acceptable salt thereof, according to claim 1, in association with a pharmaceutically-acceptable diluent or carrier.

11. A method for treating rheumatoid arthritis in a warm-blooded animal in need thereof, which comprises administering to said animal an effective amount of a compound of formula (I) or a pharmaceutically acceptable salt thereof as claimed in claim 1.

* * * * *